United States Patent
Kowalczykowski et al.

(10) Patent No.: US 7,666,591 B2
(45) Date of Patent: *Feb. 23, 2010

(54) SINGLE STRANDED DNA BINDING PROTEINS FROM ARCHAEA AND USES THEREFOR

(75) Inventors: Stephen C. Kowalczykowski, Davis, CA (US); Frédéric Chédin, Arcadia, CA (US); Erica M. Seitz, Davis, CA (US)

(73) Assignees: The Regents of the University of California, Oakland, CA (US); The United States of America as represented by the Department of Health and Human Services, Washington, DC (US)

( * ) Notice: Subject to any disclaimer, the term of this patent is extended or adjusted under 35 U.S.C. 154(b) by 269 days.

This patent is subject to a terminal disclaimer.

(21) Appl. No.: 11/035,703

(22) Filed: Jan. 14, 2005

(65) Prior Publication Data

US 2005/0164265 A1 Jul. 28, 2005

Related U.S. Application Data

(63) Continuation of application No. 09/631,616, filed on Aug. 4, 2000, now Pat. No. 6,852,832.

(60) Provisional application No. 60/147,680, filed on Aug. 6, 1999.

(51) Int. Cl.
    C12Q 1/68 (2006.01)
    C12P 19/34 (2006.01)
    C07K 14/195 (2006.01)
    C07H 21/02 (2006.01)
    C07H 21/04 (2006.01)

(52) U.S. Cl. .......................... 435/6; 435/91.2; 530/350; 530/358; 536/23.7

(58) Field of Classification Search ....................... None
    See application file for complete search history.

(56) References Cited

U.S. PATENT DOCUMENTS

| | | | |
|---|---|---|---|
| 5,449,603 | A | 9/1995 | Nielson et al. |
| 5,605,824 | A | 2/1997 | Nielson et al. |
| 5,646,019 | A | 7/1997 | Nielson et al. |
| 5,773,257 | A | 6/1998 | Nielson et al. |
| 6,503,729 | B1 | 1/2003 | Bult et al. |
| 6,852,832 | B1 | 2/2005 | Kowalczykowski et al. |
| 2004/0180342 | A1 | 9/2004 | Haseltine et al. |

OTHER PUBLICATIONS

Cubeddu, L., et al., "Structural and functional characterization of *Solfolobus solfactaricus* SSB and its interaction with DNA," FASEB Summer Research, 2002, Poster Abstract, 1 pg.

Cubeddu, L., et al., "Structural and calorimetric studies of an archaeal single-stranded DNA binding protein," European Conference on Current Trends in Microcalorimetry: Applications of Biocalorimetry (ABC III), Aug. 27-30, 2002, Dublin, Ireland, Abstract, 1 pg.

Haseltine, C., et al., "A distinctive single-stranded DNA binding protein from the Archaeon *Sulfolobus solfataricus*," Molecular Microbiology, 2002, vol. 43, No. 6, pp. 1505-1515.

Kerr, I., et al., "Overexpression, purification, crystallization and data collection of a single-stranded DNA-binding protein from *Sulfolobus solfataricus*," Acta Cryst., 2001, vol. D57, pp. 1290-1292.

Kerr, I., et al., "Insights into ssDNA Recognition by the OB Fold from a Structural and Thermodynamic Study of Sulfolobus SSB Protein;" 2003; The EMBO Journall vol. 22; No. 11; pp. 2561-2570.

She, Q., et al., "The complete genome of the crenarchaeon *Sulfolobus solfataricus* P2," PNAS, Jul. 3, 2001, vol. 98, No. 14, pp. 7835-7840.

Bochkarev, A., *Nature* 385, 176-181 (1997).

Bochkareva, E., et al., *J. Biol. Chem.* 273, 3932-3947 (1998).

Bult, C. J. et al., Science 273:1058-1073 (1996).

Bult, et al., NCBI, National Library of Medicine, NIH (Bethesda, MD, USA) Accession No. F64444, Sep. 1996.

Chedin et al., TIBS 23:273-277 (1998).

Fairman, M. P. et al., *Embo J.* 7, 1211-1218 (1988).

Gomes, X. V. *Biochemistry* 35, 10558-10568 (1996).

Henricksen, L. A., *Nucleic Acids Res.* 24, 3107-3112 (1996).

Kelly, et al., *PNAS* 95(25):14634-9 (1998).

Kim et al., Biochemistry, 33:14197-206 (1994).

Kim et al., Mol. Cell Biol., 12:3050-3059.

Klenk, H. P. et al., *Nature* 390, 364-370 (1997).

Lin, Y.-L. et al., *J. Biol. Chem.* 273, 1453-1461 (1996).

Lohman, T. M. et al., *Annu. Rev. Biochem.* 63, 527-570 (1994).

Philipova, D. et al., *Genes Dev.* 10, 2222-2233 (1996).

Sancar, A., et al., *Proc. Natl. Acad. Sci. USA* 78, 4274-4278 (1981).

Sreenivas, Biochemistry and Molecular Biology International (Feb. 1998) 44: 269-282.

Shamoo, Y. et al., *Nature* 376, 362-366 (1995).

Smith, D. R. et al. *J. Bacteriol.* 179, 7135-7155 (1996).

Wold, M. S., *Annu. Rev. Biochem.* 66, 61-92 (1997).

*Primary Examiner*—Carla Myers
(74) *Attorney, Agent, or Firm*—Townsend and Townsend and Crew LLP

(57) ABSTRACT

The invention provides ssDNA-binding proteins from three species of archaeons, *Methanococcus jannaschii*, *Methanobacter theromoautotrophicum*, and *Archaeoglobus fulgidus*, as well as the ability to identify ssDNA-binding proteins from other archaeons. The proteins help render DNA more accessible to DNA polymerase and are robust reagents for a variety of biotechnical processes, including PCR. The invention further provides nucleic acids encoding such proteins, vectors for transfecting host cells, host cells comprising the vectors, and methods of using the proteins.

8 Claims, 5 Drawing Sheets

(b)

| | | |
|---|---|---|
| A | (80-163) | ITGVITDISEIKTFKRRDGSLGKYKRITIADKSGTIRMTLWDDLAEL--DVKVGDVIKTERARA-----RKWRMNLELSSTSETKIKKL-EN |
| B | (188-271) | FEGEVISALPIKEFKRADGSIGKLKSFIVRDETGSIRVTLWDNLTDI--DVGRGDYVRVRGYIR-----EGYYGGLECTANYVEILKKG-EK |
| C | (293-382) | VKGRVIAISNKKSVDL-DGEIAKVQDIILDNGTGRVRVSFWRGKTALLENIKEGDLVRITNCRVKTFYDREGNKRTDLVATLETEVIKD-EN |
| D | (411-493) | MIAQVVEDYGVNEIEFED-KVRKVRNLLEDGTGRIRLSIWDDLAEI--EIKEGDIVEILHAYA-----KERGDYIDLVIGKYGRIIINPEG |

(c)

| | |
|---|---|
| Consensus | **G*vi*is*iKtfkr*DGsIgKvk*iil*DgTGrIRvtLWDdLaei**diKeGD*VrIara*rey*leIvat*et*iKk**En |
| MJ1159 | IkARVTnKseIRTWsN*RGE-GKLFS***L*DESGEIRATAFNDQ*DKF*diiqvkVYYfSKg*lkiankQyTnV*ELTf*reT*v**-ceD |
| Eukaryotes | |

Figure 1 (cont'd.)

```
MJ1159            DTLFLYLCP..NCRKRVVEI..DGI.YNCPICGDVEPEEILR..LNFVVDDGTGTLLCRAYDRRVEKMLKMNREELKNL
Dm RPA70 (524-595) ENAFYRACPQSDCNKKVVDEG.NDQ.FRCEKCNALFPNFKYRLLIMSIGDWTSNRWVSSFNEVGEQLLGHTSQEVGEA
Hs RPA70 (457-533) ENCMYQACPTQDCNKKVIDQQ.NGL.YRCEKCDTEFPNFKYRMILSVNIADFQENQWTCFQESAEAILGQNAYLGEL
Xl RPA70 (474-550) ENCLYQACPSQDCNKKVIDQQ.NGL.FRCEKCNKEFPNFKYRLILSANIADFGENQWITCFQESAESILGQNATYLGEL
Sp RPA70 (465-541) KNVSYPACPAADCNKKVFDQ..GGS.WRCEKCNKEYDAPQYRYITTIAVGDHTGQLWLNVFDDVGKLIMHKTADELNDL
Sc RPA70 (470-545) DNFAYPACSNEMCNKKVLEQP.DGT.WRCEKCDTNNARPNWRYLTISIIDETNQLWLTLFDDQAKQLLGVDANTLMSL
Cf RPA70 (479-555) DAQWYDACPT..CNKKVTEEGAQGDRFRCEKCDATVVPTQ.RYLVSIQVTDNVSQVWLTLFNEAGVEFFGMEASELKRR
         (306-381)
```

Figure 3

```
                         SEQUENCE LISTING

<160> NUMBER OF SEQ ID NOS: 31

<210> SEQ ID NO 1
<211> LENGTH: 645
<212> TYPE: PRT
<213> ORGANISM: Methanococcus jannaschii
<220> FEATURE:
<223> OTHER INFORMATION: MJ1159 single stranded DNA-binding
      (ssDNA-binding) protein replication protein A-related protein

<400> SEQUENCE: 1

Met Ile Gly Asp Tyr Glu Arg Phe Lys Gln Leu Lys Lys Val Ala
 1               5                  10                  15

Glu Ala Leu Asn Ile Ser Glu Glu Leu Asp Arg Met Ile Asp Lys
                20                  25                  30

Lys Ile Glu Glu Asn Gly Gly Ile Ile Leu Lys Asp Ala Ala Leu Met
            35                  40                  45

Met Ile Ala Lys Glu His Gly Val Tyr Gly Glu Glu Lys Asn Asp Glu
     50                  55                  60

Glu Phe Leu Ile Ser Asp Ile Glu Glu Gly Gln Ile Gly Val Glu Ile
 65                  70                  75                  80

Thr Gly Val Ile Thr Asp Ile Ser Glu Ile Lys Thr Phe Lys Arg Arg
                 85                  90                  95

Asp Gly Ser Leu Gly Lys Tyr Lys Arg Ile Thr Ile Ala Asp Lys Ser
                100                 105                 110

Gly Thr Ile Arg Met Thr Leu Trp Asp Asp Leu Ala Glu Leu Asp Val
            115                 120                 125

Lys Val Gly Asp Val Ile Lys Ile Glu Arg Ala Arg Ala Arg Lys Trp
    130                 135                 140

Arg Asn Asn Leu Glu Leu Ser Ser Thr Ser Glu Thr Lys Ile Lys Lys
145                 150                 155                 160

Leu Glu Asn Tyr Glu Gly Glu Leu Pro Glu Ile Lys Asp Thr Tyr Asn
                165                 170                 175

Ile Gly Glu Leu Ser Pro Gly Met Thr Ala Thr Phe Glu Gly Glu Val
            180                 185                 190

Ile Ser Ala Leu Pro Ile Lys Glu Phe Lys Arg Ala Asp Gly Ser Ile
            195                 200                 205

Gly Lys Leu Lys Ser Phe Ile Val Arg Asp Glu Thr Gly Ser Ile Arg
    210                 215                 220

Val Thr Leu Trp Asp Asn Leu Thr Asp Ile Asp Val Gly Arg Gly Asp
225                 230                 235                 240

Tyr Val Arg Val Arg Gly Tyr Ile Arg Glu Gly Tyr Tyr Gly Gly Leu
                245                 250                 255

Glu Cys Thr Ala Asn Tyr Val Glu Ile Leu Lys Lys Gly Glu Lys Ile
                260                 265                 270

Glu Ser Glu Glu Val Asn Ile Glu Asp Leu Thr Lys Tyr Glu Asp Gly
            275                 280                 285
```

```
Glu Leu Val Ser Val Lys Gly Arg Val Ile Ala Ile Ser Asn Lys Lys
    290                 295                 300

Ser Val Asp Leu Asp Gly Glu Ile Ala Lys Val Gln Asp Ile Ile Leu
305                 310                 315                 320

Asp Asn Gly Thr Gly Arg Val Arg Val Ser Phe Trp Arg Gly Lys Thr
                325                 330                 335

Ala Leu Leu Glu Asn Ile Lys Glu Gly Asp Leu Val Arg Ile Thr Asn
            340                 345                 350

Cys Arg Val Lys Thr Phe Tyr Asp Arg Glu Gly Asn Lys Arg Thr Asp
        355                 360                 365

Leu Val Ala Thr Leu Glu Thr Glu Val Ile Lys Asp Glu Asn Ile Glu
370                 375                 380

Ala Pro Glu Tyr Glu Leu Lys Tyr Cys Lys Ile Glu Asp Ile Tyr Asn
385                 390                 395                 400

Arg Asp Val Asp Trp Asn Asp Ile Asn Leu Ile Ala Gln Val Val Glu
                405                 410                 415

Asp Tyr Gly Val Asn Glu Ile Glu Phe Glu Asp Lys Val Arg Lys Val
            420                 425                 430

Arg Asn Leu Leu Leu Glu Asp Gly Thr Gly Arg Ile Arg Leu Ser Leu
        435                 440                 445

Trp Asp Asp Leu Ala Glu Ile Glu Ile Lys Glu Gly Asp Ile Val Glu
450                 455                 460

Ile Leu His Ala Tyr Ala Lys Glu Arg Gly Asp Tyr Ile Asp Leu Val
465                 470                 475                 480

Ile Gly Lys Tyr Gly Arg Ile Ile Asn Pro Glu Gly Val Glu Ile
                485                 490                 495

Lys Thr Asn Arg Lys Phe Ile Ala Asp Ile Glu Asp Gly Glu Thr Val
            500                 505                 510

Glu Val Arg Gly Ala Val Val Lys Ile Leu Ser Asp Thr Leu Phe Leu
        515                 520                 525

Tyr Leu Cys Pro Asn Cys Arg Lys Arg Val Val Glu Ile Asp Gly Ile
530                 535                 540

Tyr Asn Cys Pro Ile Cys Gly Asp Val Glu Pro Glu Glu Ile Leu Arg
545                 550                 555                 560

Leu Asn Phe Val Val Asp Asp Gly Thr Gly Thr Leu Leu Cys Arg Ala
                565                 570                 575

Tyr Asp Arg Arg Val Glu Lys Met Leu Lys Met Asn Arg Glu Glu Leu
            580                 585                 590

Lys Asn Leu Thr Ile Glu Met Val Glu Asp Glu Ile Leu Gly Glu Glu
        595                 600                 605

Phe Val Leu Tyr Gly Asn Val Arg Val Glu Asn Asp Glu Leu Ile Met
610                 615                 620

Val Val Arg Arg Val Asn Asp Val Asp Val Glu Lys Glu Ile Arg Ile
625                 630                 635                 640

Leu Glu Glu Met Glu
                645

<210> SEQ ID NO 2
<211> LENGTH: 1935
<212> TYPE: DNA
<213> ORGANISM: Methanococcus jannaschii
<220> FEATURE:
<223> OTHER INFORMATION: MJ1159 single stranded DNA-binding
      (ssDNA-binding) protein replication protein A-related protein

<400> SEQUENCE: 2
```

-continued

```
atgataggag attatgaaag atttaaacaa ctcaaaaaaa aggttgctga agcattgaat     60
attagtgagg aggaattaga taggatgatt gataaaaaaa ttgaagaaaa cggaggaata    120
atattgaaag atgctgcatt aatgatgatt gcaaaagaac atggagttta tggagaagaa    180
aaaaatgatg aagaattttt aattagtgat attgaagagg gacagatagg cgttgagata    240
actggagtta taactgatat ctctgaaata aaaacattca aaaggagaga tgggagttta    300
gggaaataca aaagaattac aatagcggat aagtcaggaa ctataagaat gactttatgg    360
gacgatttgg ctgaattaga tgtaaaagtt ggagatgtta ttaaaattga aagagcaaga    420
gcaagaaaat ggagaaataa tttagagttg agttcaacat ctgaaactaa gattaaaaaa    480
ttagaaaact atgaaggaga acttccagag attaaagata cctacaatat tggtgagcta    540
agtcctggaa tgacagcaac atttgaagga gaagttatct cagctcttcc aatcaaagaa    600
tttaaaagag ctgatggtag tattggaaaa ttaaaatcat ttattgttag agatgagaca    660
ggaagtataa gagttacctt atgggataat ctaacagata tcgatgttgg tagaggagat    720
tacgttagag ttaggggcta tataagggaa ggttattatg gggtttaga atgcaccgca     780
aattatgtag agatattaaa aaaaggagaa aaaatagaga gtgaagaagt aaatattgag    840
gatttaacaa aatatgaaga tggagaactg gtgagtgtta aaggtagagt tatagccata    900
agtaataaaa aaagcgtaga tttggatgga gagatagcaa aggttcaaga tattatatta    960
gataacggca ctggtagagt tagagtttca ttttggagag gaaaaactgc tttattggaa   1020
aatataaaag aaggggactt agttagaata acaaactgta gagttaagac gttttatgat   1080
agagaaggaa ataaaagaac tgatttagtt gccacattag aaacagaagt tattaaagat   1140
gaaaacattg aagctccaga gtatgagcta aaatattgca aaattgaaga tatttataat   1200
agagatgttg actggaacga tataaattta atagctcaag ttgttgagga ttatggagtt   1260
aatgaaattg aatttgaaga taaggttaga aaagtaagaa atttattgtt agaagatgga   1320
actggaagaa taaggttgag tttatgggat gatttggctg aaatagagat taaagaagga   1380
gatattgtag aaattttaca tgcctatgct aaggagaggg gagattatat agatttggtt   1440
attggaaaat atggaagaat aattataaat ccagaagggg ttgaaataaa aaccaataga   1500
aagtttatag cagatattga agacggagaa actgttgaag ttagaggggc tgtagttaag   1560
atattgagtg acactctctt tctttattta tgcccaaatt gtagaaagag ggttgtagag   1620
attgatggaa tttataactg ccctatttgt ggagatgttg agccagaaga gattttaaga   1680
ttgaattttg ttgtagatga tgggactgga actttattat gtagggctta tgatagaaga   1740
gttgagaaga tgttaaaaat gaatagggag gagttaaaga acctaactat agaaatggtg   1800
gaagatgaaa tattagggga agagtttgtt ttgtatggaa atgttagagt agagaatgat   1860
gaattaatta tggttgttag aagagttaat gatgtagatg ttgagaaaga aataagaata   1920
ttggaggaaa tggaa                                                    1935
```

<210> SEQ ID NO 3
<211> LENGTH: 543
<212> TYPE: DNA
<213> ORGANISM: Methanobacterium thermoautotrophicum
<220> FEATURE:
<223> OTHER INFORMATION: MTH1384 single stranded DNA-binding
(ssDNA-binding) protein replication factor A
related protein

<400> SEQUENCE: 3

-continued

```
atgaaattat ccatcggcaa ttcaagtaga atagagccag ctagtgaacg tgatctcgaa      60
ggattaccga gttttgatga attacaagaa atgctatatc cccatcgtga catcgccgat     120
ctagacgagg attcgagaaa cgtcttgatc gagggagaat tgatagagat gtcaggacgc     180
agaatcctga gtatcaaatg tccatcgtgt aacgaaaggc tcgacctatc tgatgaaaat     240
atttgcaatt tttgcggcga gcttgtggac gagccacggt acttgcttat gattccagga     300
cgaattatgg atgataccgg tgaggttatg ataacattct tgggagaga agcagaatcc     360 atactcgaaa tgacaacgga cgaagtagtg aatataatta tcagagcgc ggacgagtct      420 gcattagagg aacgggtcga agaccttaac ggggtaactg tgcgagttat aggtaacgca     480
gatatggacg tatatagcga ggagctgagg ttcattcctc gcaaagtcgt taagaaggag     540
ctg                                                                   543
```

<210> SEQ ID NO 4
<211> LENGTH: 1866
<212> TYPE: DNA
<213> ORGANISM: Methanobacterium thermoautotrophicum
<220> FEATURE:
<223> OTHER INFORMATION: MTH1385 single stranded DNA-binding
    (ssDNA-binding) protein replication factor A
    related protein

<400> SEQUENCE: 4

```
atgaaggaag aacttaagag ggagtatgag agaataaagg accggataag tccggaggag      60
tttgaagagt tgatcgaaaa gaagaaggag gagttgggag acattgggtt catggatgac     120
ttaacaatcg catcgaccgt ggtagacgat atacttaaag agaaaaacac aatgttatcc     180
gaaaaaccag agcatcgcat ggacaccatc agtaagctag aggagggtgc tgaaacccct     240
gtaacgggaa gggtcatgaa aatcagctct ccacgcactt ttacaacaag aaagggacgg     300
gaggggaaat tggcgaacgt aataattgcc gacgatacgg gtgaactgag ggctgtattt     360
tggacagaaa atatcaaact gttaaaaaaa tttcgtgagg gggacgtaat aagaatcaaa     420
gatgtcaaca tccgggggagg cttcggggggt cgaaaagagg ctcaccttat gccacgtagc     480
acggtcgaag tactagatcc tgaggattat cctgaattcc ctgagtatcg ggaggaaatt     540
acacccatcg ggaccctcgt ggaggatgac gaagttaatg ttatcgctcg cattaccgga     600
gtaagcagag tgcgaacttt cgaaagagac ggccgcgagg ccgatttat atccctggat      660 ataatggatg caacaggctc gaccacttac acgctctgga ataacgatgt taacctggtt     720
gaggaactcg gtctaaaaga aggagacgcc gttaaaattt tgtgggccca gccccgccgg     780
cgcgacgata aagtgacact cacccatacg tcacttactc gtgttgtccc gggagaatat     840
gacgtaccag aatttaggga gagctcgtg aagatagggg acctacatga gatgcgaaat      900
gttacggtaa tgggcttagt tacaaaggtc aatgatcccg tggaattcga agaaatgac      960 gggactactg gctctgtcaa atcaatcgaa atagcggatg atacagggtc cgctcgagtg    1020
acattatggg atgaggacac ccgaatcaag attaataaag gcgacatcat tcggattagt    1080
ggagcaaatg tcgagttcga tgacttcaac caaagctatc gaattaacac taacttcaat    1140
actcgtataa ccttaaaccc cgaaagtgac ggtgcgttac ttaaggtttt agaagagtac    1200
agagagcaga tgaggccgat gaaatatatct gaatttttag aaatgaagaa tgagggagag    1260
gaggtagatg tggtgggtcg tatcttctca ctatcggacc cgagggaatt tgaacgggag    1320
gatgggactg gaatagtaag atctatggag ttggccgatg aaacaggaaa aatacgcatt    1380
tcactgtggg atgaaaaagc cgagaaaccc atgaatatag gtgatgctgt tagaatcgag    1440
```

-continued

```
aacgcacgta ttcgtctggg cctatacagt gtggaattga gtgcgggcag gacgaccagg    1500
atagttaacc ccctccctga agatatggaa gaccttccgt cgtttgaaga gcttgaagag    1560
atgctctacc agaccaagaa gatcgcagac ttagaggaag acgacaggaa tattcgcatt    1620
attgcgcggg tcgtggacct gtttgagcca agagagtttc aacggggcga cggtacgcct    1680
ggtttagtaa gaactgcaga atttgcagac gatacgggt ccatacgcgc cagtttgtgg     1740
gatgatgcgg cagaaaagcc gctaagtatc ggtgatccag tgaagattga gaatccacga    1800
gtcgtcttcc gtgatgacat gggcggtggg cgattagaaa cgcaacaccg taagcaattc    1860
aaggat                                                               1866
```

<210> SEQ ID NO 5
<211> LENGTH: 181
<212> TYPE: PRT
<213> ORGANISM: Methanobacterium thermoautotrophicum
<220> FEATURE:
<223> OTHER INFORMATION: MTH1384 single stranded DNA-binding
      (ssDNA-binding) protein replication factor A
      related protein

<400> SEQUENCE: 5

```
Met Lys Leu Ser Ile Gly Asn Ser Ser Arg Ile Glu Pro Ala Ser Glu
 1               5                  10                  15

Arg Asp Leu Glu Gly Leu Pro Ser Phe Asp Glu Leu Gln Glu Met Leu
            20                  25                  30

Tyr Pro His Arg Asp Ile Ala Asp Leu Asp Glu Asp Ser Arg Asn Val
        35                  40                  45

Leu Ile Glu Gly Glu Leu Ile Glu Met Ser Gly Arg Arg Ile Leu Ser
    50                  55                  60

Ile Lys Cys Pro Ser Cys Asn Glu Arg Leu Asp Leu Ser Asp Glu Asn
65                  70                  75                  80

Ile Cys Asn Phe Cys Gly Glu Leu Val Asp Glu Pro Arg Tyr Leu Leu
                85                  90                  95

Met Ile Pro Gly Arg Ile Met Asp Asp Thr Gly Glu Val Met Ile Thr
            100                 105                 110

Phe Phe Gly Arg Glu Ala Glu Ser Ile Leu Glu Met Thr Thr Asp Glu
        115                 120                 125

Val Val Asn Ile Ile Asn Gln Ser Ala Asp Glu Ser Ala Leu Glu Glu
    130                 135                 140

Arg Val Glu Asp Leu Asn Gly Val Thr Val Arg Val Ile Gly Asn Ala
145                 150                 155                 160

Asp Met Asp Val Tyr Ser Glu Glu Leu Arg Phe Ile Pro Arg Lys Val
                165                 170                 175

Val Lys Lys Glu Leu
            180
```

<210> SEQ ID NO 6
<211> LENGTH: 622
<212> TYPE: PRT
<213> ORGANISM: Methanobacterium thermoautotrophicum
<220> FEATURE:
<223> OTHER INFORMATION: MTH1385 single stranded DNA-binding
      (ssDNA-binding) protein replication factorA
      related protein

<400> SEQUENCE: 6

```
Met Lys Glu Glu Leu Lys Arg Glu Tyr Glu Arg Ile Lys Asp Arg Ile
 1               5                  10                  15
```

-continued

Ser Pro Glu Glu Phe Glu Leu Ile Glu Lys Lys Glu Leu
        20                  25                  30

Gly Asp Ile Gly Phe Met Asp Leu Thr Ile Ala Ser Thr Val Val
        35                  40                  45

Asp Asp Ile Leu Lys Glu Lys Asn Thr Met Leu Ser Glu Lys Pro Glu
50                  55                  60

His Arg Met Asp Thr Ile Ser Lys Leu Glu Gly Ala Glu Thr Pro
65                  70                  75                  80

Val Thr Gly Arg Val Met Lys Ile Ser Ser Pro Arg Thr Phe Thr Thr
                85                  90                  95

Arg Lys Gly Arg Glu Gly Lys Leu Ala Asn Val Ile Ile Ala Asp Asp
                100                 105                 110

Thr Gly Glu Leu Arg Ala Val Phe Trp Thr Glu Asn Ile Lys Leu Leu
            115                 120                 125

Lys Lys Phe Arg Glu Gly Asp Val Ile Arg Ile Lys Asp Val Asn Ile
130                 135                 140

Arg Gly Gly Phe Gly Gly Arg Lys Glu Ala His Leu Met Pro Arg Ser
145                 150                 155                 160

Thr Val Glu Val Leu Asp Pro Glu Asp Tyr Pro Glu Phe Pro Glu Tyr
                165                 170                 175

Arg Glu Glu Ile Thr Pro Ile Gly Asp Leu Val Glu Asp Glu Val
                180                 185                 190

Asn Val Ile Ala Arg Ile Thr Gly Val Ser Arg Val Arg Thr Phe Glu
            195                 200                 205

Arg Asp Gly Arg Glu Gly Arg Phe Ile Ser Leu Asp Ile Met Asp Ala
210                 215                 220

Thr Gly Ser Thr Thr Tyr Thr Leu Trp Asn Asn Asp Val Asn Leu Val
225                 230                 235                 240

Glu Glu Leu Gly Leu Lys Glu Gly Asp Ala Val Lys Ile Leu Trp Ala
                245                 250                 255

Gln Pro Arg Arg Arg Asp Asp Lys Val Thr Leu Thr His Thr Ser Leu
            260                 265                 270

Thr Arg Val Val Pro Gly Glu Tyr Asp Val Pro Glu Phe Arg Glu Glu
        275                 280                 285

Leu Val Lys Ile Gly Asp Leu His Glu Met Arg Asn Val Thr Val Met
            290                 295                 300

Gly Leu Val Thr Lys Val Asn Asp Pro Val Glu Phe Glu Arg Asn Asp
305                 310                 315                 320

Gly Thr Thr Gly Ser Val Lys Ser Ile Glu Ile Ala Asp Asp Thr Gly
                325                 330                 335

Ser Ala Arg Val Thr Leu Trp Asp Glu Asp Thr Arg Ile Lys Ile Asn
            340                 345                 350

Lys Gly Asp Ile Ile Arg Ile Ser Gly Ala Asn Val Glu Phe Asp Asp
                355                 360                 365

Phe Asn Gln Ser Tyr Arg Ile Asn Thr Asn Phe Asn Thr Arg Ile Thr
        370                 375                 380

Leu Asn Pro Glu Ser Asp Gly Ala Leu Leu Lys Val Leu Glu Glu Tyr
385                 390                 395                 400

Arg Glu Gln Met Arg Pro Met Lys Ile Ser Glu Ile Leu Glu Met Glu
                405                 410                 415

Asp Glu Gly Glu Glu Val Asp Val Val Gly Arg Ile Phe Ser Leu Ser
            420                 425                 430

```
Asp Pro Arg Glu Phe Glu Arg Glu Asp Gly Thr Gly Ile Val Arg Ser
        435                 440                 445

Met Glu Leu Ala Asp Glu Thr Gly Lys Ile Arg Ile Ser Leu Trp Asp
    450                 455                 460

Glu Lys Ala Glu Lys Pro Met Asn Ile Gly Asp Ala Val Arg Ile Glu
465                 470                 475                 480

Asn Ala Arg Ile Arg Leu Gly Leu Tyr Ser Val Glu Leu Ser Ala Gly
                485                 490                 495

Arg Thr Thr Arg Ile Val Asn Pro Leu Pro Glu Asp Met Glu Asp Leu
            500                 505                 510

Pro Ser Phe Glu Glu Leu Glu Glu Met Leu Tyr Gln Thr Lys Lys Ile
        515                 520                 525

Ala Asp Leu Glu Glu Asp Asp Arg Asn Ile Arg Ile Ile Ala Arg Val
    530                 535                 540

Val Asp Leu Phe Glu Pro Arg Glu Phe Gln Arg Gly Asp Gly Thr Pro
545                 550                 555                 560

Gly Leu Val Arg Thr Ala Glu Phe Ala Asp Asp Thr Gly Ser Ile Arg
                565                 570                 575

Ala Ser Leu Trp Asp Asp Ala Ala Glu Lys Pro Leu Ser Ile Gly Asp
            580                 585                 590

Pro Val Lys Ile Glu Asn Pro Arg Val Val Phe Arg Asp Asp Met Gly
        595                 600                 605

Gly Gly Arg Leu Glu Thr Gln His Arg Lys Gln Phe Lys Asp
    610                 615                 620

<210> SEQ ID NO 7
<211> LENGTH: 708
<212> TYPE: DNA
<213> ORGANISM: Archaeoglobus fulgidus
<220> FEATURE:
<223> OTHER INFORMATION: AF0382 homolog of N-terminus of MJ1159

<400> SEQUENCE: 7
gtgggggctg tttctgcttt tcttgggct  tcttctggca ggctacatgc actggaggtt     60
ttcgttatga agattccaaa aacgtatgat gagataatgg agcatttcgg cgggcttatt    120
gatgaggtga ccgcggaact gctcgaaagc tacgcaaagg gagaaactgt gagggtgagt    180
gaggcgttgg ccaaaagcgg cagagttgcc gttgaaggcg tggttttgag ggttttttcc    240
gtaaggcatt tcagcaaaaa cggcaggagc ggaaaggttg gaagcgttgt aattcaggac    300
gactgcacgg ttagagttaa cttctggaat gaggcggcag agataataga ggctggggat    360
attgtggaag gagcgaggat aaaagtaagg ggctatgcga ggggggagga gatacacgtc    420
aacagcctct cggaggtgga ggttttgtc gactttgtaa atatctctga gcttgatgag    480
aaggttgggg agagggtaaa cgtaaagggc tttgtatccg gactgggtga gccggaaaag    540
gccaatgaaa tatacatttc agatgagact ggcagagtga aggttttact ggaaaatgag    600
agcctctact atgccgttga cattgggtcc tacgttgaga tatacaacgc tctggccgga    660
gaggatggca tttacgtcga tagaaattcg aggttcagtg ttggggag              708

<210> SEQ ID NO 8
<211> LENGTH: 936
<212> TYPE: DNA
<213> ORGANISM: Archaeoglobus fulgidus
<220> FEATURE:
<223> OTHER INFORMATION: AF0780 homolog of C-terminus of MJ1159

<400> SEQUENCE: 8
```

```
atggacagag ttgagagttt agccaaccag attttttgaag attacaagga ttatggagtt    60
gacagaaagg agattgttga gaagctcaga aaacttctta tcgagttcag agttccggaa   120
aatgaagctg ttagaaccat cagaaattac atcatcaggg agtacggagc acctgcaacg   180
gtaaggaggg agaggattac aaaaattgag gaaataaagg agccgaacaa atgggttacg   240
gtgaaggcca aggtcattca gctttgggag agcagcagcc cctcaatagc ccaggtgggg   300
ttgattggtg atgaaaccgg ctacatcagg tttctcgtgt ggacgaaggc caagaagcag   360
ccagttgatg agggtaaaag ctacatattc aggaacgttg ttgttgacga ctacggggga   420
gttttaaggc ttaacgtaac gaaaataagc gagatagagg agattgagga ggatgtgaag   480
gtcaaaccgc cggaagagct gagcgaggac gtggaggtcg ttggggcgct tgtagcgatt   540
cagcagaaca gcggactcat tcagcgctgc agcgttgagg gctgcaacag agtgataaag   600
atggggaagt gtccggaaca cggaaaaacg aaggcgaaag acgatttgag gattaaagga   660
gtgcttgacg acggatacag aacctacgag gttatcataa acgaggaggg tgtggaatct   720
ctgaccggaa ttaaccttga gaaggcaaag aaaatagccg aggaaacttt ggatagaggt   780
gcggttctga cagaacttaa gaaaatgctt ctcggaaagt acctgagggt tgttggcacc   840
gcaacgccga gatacctgat agccaagcat gttgagttct tcagaccaga tatcagaaag   900
gagattgaga aggttaaagc ccttctggag gaggta                             936
```

<210> SEQ ID NO 9
<211> LENGTH: 236
<212> TYPE: PRT
<213> ORGANISM: Archaeoglobus fulgidus
<220> FEATURE:
<221> NAME/KEY: MOD_RES
<222> LOCATION: (1)
<223> OTHER INFORMATION: AF0382 homolog of N-terminus of MJ1159
<223> OTHER INFORMATION: Xaa = Val or Met

<400> SEQUENCE: 9

Xaa Gly Ala Val Ser Ala Phe Ser Trp Ala Ser Ser Gly Arg Leu His
  1               5                  10                  15

Ala Leu Glu Val Phe Val Met Lys Ile Pro Lys Thr Tyr Asp Glu Ile
             20                  25                  30

Met Glu His Phe Gly Gly Leu Ile Asp Glu Val Thr Ala Glu Leu Leu
         35                  40                  45

Glu Ser Tyr Ala Lys Gly Glu Thr Val Arg Val Ser Glu Ala Leu Ala
     50                  55                  60

Lys Ser Gly Arg Val Ala Val Glu Gly Val Val Leu Arg Val Phe Pro
 65                  70                  75                  80

Val Arg His Phe Ser Lys Asn Gly Arg Ser Gly Lys Val Gly Ser Val
                 85                  90                  95

Val Ile Gln Asp Asp Cys Thr Val Arg Val Asn Phe Trp Asn Glu Ala
            100                 105                 110

Ala Glu Ile Ile Glu Ala Gly Asp Ile Val Glu Gly Ala Arg Ile Lys
        115                 120                 125

Val Arg Gly Tyr Ala Arg Gly Glu Glu Ile His Val Asn Ser Leu Ser
    130                 135                 140

Glu Val Glu Val Phe Val Asp Phe Val Asn Ile Ser Glu Leu Asp Glu
145                 150                 155                 160

Lys Val Gly Glu Arg Val Asn Val Lys Gly Phe Val Ser Gly Leu Gly
                165                 170                 175

```
Glu Pro Glu Lys Ala Asn Glu Ile Tyr Ile Ser Asp Glu Thr Gly Arg
            180                 185                 190

Val Lys Val Leu Leu Glu Asn Glu Ser Leu Tyr Tyr Ala Val Asp Ile
        195                 200                 205

Gly Ser Tyr Val Glu Ile Tyr Asn Ala Leu Ala Gly Asp Gly Ile
        210                 215                 220

Tyr Val Asp Arg Asn Ser Arg Phe Ser Val Gly Glu
225                 230                 235

<210> SEQ ID NO 10
<211> LENGTH: 312
<212> TYPE: PRT
<213> ORGANISM: Archaeoglobus fulgidus
<220> FEATURE:
<223> OTHER INFORMATION: AF0780 homolog of C-terminus of MJ1159

<400> SEQUENCE: 10

Met Asp Arg Val Glu Ser Leu Ala Asn Gln Ile Phe Glu Asp Tyr Lys
  1               5                  10                  15

Asp Tyr Gly Val Asp Arg Lys Glu Ile Val Glu Lys Leu Arg Lys Leu
             20                  25                  30

Leu Ile Glu Phe Arg Val Pro Glu Asn Glu Ala Val Arg Thr Ile Arg
         35                  40                  45

Asn Tyr Ile Ile Arg Glu Tyr Gly Ala Pro Ala Thr Val Arg Arg Glu
     50                  55                  60

Arg Ile Thr Lys Ile Glu Glu Ile Lys Glu Pro Asn Lys Trp Val Thr
 65                  70                  75                  80

Val Lys Ala Lys Val Ile Gln Leu Trp Glu Ser Ser Pro Ser Ile
                 85                  90                  95

Ala Gln Val Gly Leu Ile Gly Asp Glu Thr Gly Tyr Ile Arg Phe Leu
            100                 105                 110

Val Trp Thr Lys Ala Lys Lys Gln Pro Val Asp Glu Gly Lys Ser Tyr
        115                 120                 125

Ile Phe Arg Asn Val Val Asp Asp Tyr Gly Gly Val Leu Arg Leu
        130                 135                 140

Asn Val Thr Lys Ile Ser Glu Ile Glu Glu Ile Glu Asp Val Lys
145                 150                 155                 160

Val Lys Pro Pro Glu Glu Leu Ser Glu Asp Val Glu Val Gly Ala
                165                 170                 175

Leu Val Ala Ile Gln Gln Asn Ser Gly Leu Ile Gln Arg Cys Ser Val
            180                 185                 190

Glu Gly Cys Asn Arg Val Ile Lys Met Gly Lys Cys Pro Glu His Gly
        195                 200                 205

Lys Thr Lys Ala Lys Asp Asp Leu Arg Ile Lys Gly Val Leu Asp Asp
        210                 215                 220

Gly Tyr Arg Thr Tyr Glu Val Ile Ile Asn Glu Glu Gly Val Glu Ser
225                 230                 235                 240

Leu Thr Gly Ile Asn Leu Glu Lys Ala Lys Lys Ile Ala Glu Glu Thr
                245                 250                 255

Leu Asp Arg Gly Ala Val Leu Thr Glu Leu Lys Lys Met Leu Leu Gly
            260                 265                 270

Lys Tyr Leu Arg Val Val Gly Thr Ala Thr Pro Arg Tyr Leu Ile Ala
        275                 280                 285

Lys His Val Glu Phe Phe Arg Pro Asp Ile Arg Lys Glu Ile Glu Lys
        290                 295                 300
```

Val Lys Ala Leu Leu Glu Glu Val
305                 310

<210> SEQ ID NO 11
<211> LENGTH: 218
<212> TYPE: PRT
<213> ORGANISM: Methanococcus jannaschii
<220> FEATURE:
<223> OTHER INFORMATION: MJ1159 80-297

<400> SEQUENCE: 11

Ile Thr Gly Val Ile Thr Asp Ile Ser Glu Ile Lys Thr Phe Lys Arg
1               5                   10                  15

Arg Asp Gly Ser Leu Gly Lys Tyr Lys Arg Ile Thr Ile Ala Asp Lys
            20                  25                  30

Ser Gly Thr Ile Arg Met Thr Leu Trp Asp Leu Ala Glu Leu Asp
        35                  40                  45

Val Lys Val Gly Asp Val Ile Lys Ile Glu Arg Ala Arg Ala Arg Lys
    50                  55                  60

Trp Arg Asn Asn Leu Glu Leu Ser Ser Thr Glu Thr Lys Ile Lys
65              70                  75                  80

Lys Leu Glu Asn Tyr Glu Gly Glu Leu Pro Glu Ile Lys Asp Thr Tyr
                85                  90                  95

Asn Ile Gly Glu Leu Ser Pro Gly Met Thr Ala Thr Phe Glu Gly Glu
            100                 105                 110

Val Ile Ser Ala Leu Pro Ile Lys Glu Phe Lys Arg Ala Asp Gly Ser
        115                 120                 125

Ile Gly Lys Leu Lys Ser Phe Ile Val Arg Asp Glu Thr Gly Ser Ile
130                 135                 140

Arg Val Thr Leu Trp Asp Asn Leu Thr Asp Ile Asp Val Gly Arg Gly
145                 150                 155                 160

Asp Tyr Val Arg Val Arg Gly Tyr Ile Arg Glu Gly Tyr Tyr Gly Gly
                165                 170                 175

Leu Glu Cys Thr Ala Asn Tyr Val Glu Ile Leu Lys Lys Gly Glu Lys
            180                 185                 190

Ile Glu Ser Glu Glu Val Asn Ile Glu Asp Leu Thr Lys Tyr Glu Asp
        195                 200                 205

Gly Glu Leu Val Ser Val Lys Gly Arg Val
    210                 215

<210> SEQ ID NO 12
<211> LENGTH: 232
<212> TYPE: PRT
<213> ORGANISM: Drosophila melanogaster
<220> FEATURE:
<223> OTHER INFORMATION: RPA70 181-412

<400> SEQUENCE: 12

Ile Lys Ala Arg Val Thr Ser Lys Ser Gly Ile Arg Thr Trp Ser Asn
1               5                   10                  15

Ala Arg Gly Glu Gly Lys Leu Phe Ser Met Asp Leu Met Asp Glu Ser
            20                  25                  30

Gly Glu Ile Arg Ala Thr Ala Phe Lys Glu Gln Cys Asp Lys Phe Tyr
        35                  40                  45

Asp Leu Ile Gln Val Asp Ser Val Tyr Tyr Ile Ser Lys Cys Gln Leu
    50                  55                  60

Lys Pro Ala Asn Lys Gln Tyr Ser Ser Leu Asn Asn Ala Tyr Glu Met
65              70                  75                  80

```
Thr Phe Ser Gly Glu Thr Val Val Gln Leu Cys Glu Asp Thr Asp Asp
                85                  90                  95
Asp Pro Ile Pro Glu Ile Lys Tyr Asn Leu Val Pro Ile Ser Asp Val
                100                 105                 110
Ser Gly Met Glu Asn Lys Ala Ala Val Asp Thr Ile Gly Ile Cys Lys
            115                 120                 125
Glu Val Gly Glu Leu Gln Ser Phe Val Ala Arg Thr Thr Asn Lys Glu
        130                 135                 140
Phe Lys Lys Arg Asp Ile Thr Leu Val Asp Met Ser Asn Ser Ala Ile
145                 150                 155                 160
Ser Leu Thr Leu Trp Gly Asp Asp Ala Val Asn Phe Asp Gly His Val
                165                 170                 175
Gln Pro Val Ile Leu Val Lys Gly Thr Arg Ile Asn Glu Phe Asn Gly
                180                 185                 190
Gly Lys Ser Leu Ser Leu Gly Gly Ser Ile Met Lys Ile Asn Pro
            195                 200                 205
Asp Ile Pro Glu Ala His Lys Leu Arg Gly Trp Phe Asp Asn Gly Gly
    210                 215                 220
Gly Asp Ser Val Ala Asn Met Val
225                 230

<210> SEQ ID NO 13
<211> LENGTH: 229
<212> TYPE: PRT
<213> ORGANISM: Homo sapiens
<220> FEATURE:
<223> OTHER INFORMATION: RPA70 198-427

<400> SEQUENCE: 13

Ile Cys Ala Arg Val Thr Asn Lys Ser Gln Ile Arg Thr Trp Ser Asn
1               5                   10                  15
Ser Arg Gly Glu Gly Lys Leu Phe Ser Leu Glu Leu Val Asp Glu Ser
            20                  25                  30
Gly Glu Ile Arg Ala Thr Ala Phe Asn Glu Gln Val Asp Lys Phe Phe
        35                  40                  45
Pro Leu Ile Glu Val Asn Lys Val Tyr Tyr Phe Ser Lys Gly Thr Leu
    50                  55                  60
Lys Ile Ala Asn Lys Gln Phe Thr Ala Val Lys Asn Asp Tyr Glu Met
65                  70                  75                  80
Thr Phe Asn Asn Glu Thr Ser Val Met Pro Cys Glu Asp Asp His His
                85                  90                  95
Leu Pro Thr Val Gln Phe Asp Phe Thr Gly Ile Asp Asp Leu Glu Asn
                100                 105                 110
Lys Ser Lys Asp Ser Leu Val Asp Ile Ile Gly Ile Cys Lys Ser Tyr
            115                 120                 125
Glu Asp Ala Thr Lys Ile Thr Val Arg Ser Asn Asn Arg Glu Val Ala
        130                 135                 140
Lys Arg Asn Ile Tyr Leu Met Asp Thr Ser Gly Lys Val Val Thr Ala
145                 150                 155                 160
Thr Leu Trp Gly Glu Asp Ala Asp Lys Phe Asp Gly Ser Arg Gln Pro
                165                 170                 175
Val Leu Ala Ile Lys Gly Ala Arg Val Ser Asp Phe Gly Gly Arg Ser
                180                 185                 190
Leu Ser Val Leu Ser Ser Ser Thr Ile Ile Ala Asn Pro Asp Ile Pro
            195                 200                 205
```

```
Glu Ala Tyr Lys Leu Arg Gly Trp Phe Asp Ala Glu Gly Gln Ala Leu
    210                 215                 220

Asp Gly Val Ser Ile
225

<210> SEQ ID NO 14
<211> LENGTH: 229
<212> TYPE: PRT
<213> ORGANISM: Xenopus laevis
<220> FEATURE:
<223> OTHER INFORMATION: RPA70 190-418

<400> SEQUENCE: 14

Val Arg Ala Arg Val Thr Asn Lys Gly Gln Ile Arg Thr Trp Ser Asn
  1               5                  10                  15

Ser Arg Gly Glu Gly Lys Leu Phe Ser Ile Glu Met Val Asp Glu Ser
             20                  25                  30

Gly Glu Ile Arg Ala Thr Ala Phe Asn Glu Gln Ala Asp Lys Phe Phe
         35                  40                  45

Ser Ile Ile Glu Val Asn Lys Val Tyr Tyr Phe Ser Lys Gly Thr Leu
     50                  55                  60

Lys Ile Ala Asn Lys Gln Tyr Thr Ser Val Lys Asn Asp Tyr Glu Met
 65                  70                  75                  80

Thr Phe Asn Ser Glu Thr Ser Val Ile Pro Cys Asp Asp Ser Ala Asp
                 85                  90                  95

Val Pro Met Val Gln Phe Glu Phe Val Ser Ile Gly Glu Leu Glu Ser
            100                 105                 110

Lys Asn Lys Asp Thr Val Leu Asp Ile Ile Gly Val Cys Lys Asn Val
        115                 120                 125

Glu Glu Val Thr Lys Val Thr Ile Lys Ser Asn Asn Arg Glu Val Ser
    130                 135                 140

Lys Arg Ser Ile His Leu Met Asp Ser Ser Gly Lys Val Val Ser Thr
145                 150                 155                 160

Thr Leu Trp Gly Glu Asp Ala Asp Lys Phe Asp Gly Ser Arg Gln Pro
                165                 170                 175

Val Val Ala Ile Lys Gly Ala Arg Leu Ser Asp Phe Gly Gly Arg Ser
            180                 185                 190

Leu Ser Val Leu Ser Ser Thr Val Met Ile Asn Pro Asp Ile Pro
        195                 200                 205

Glu Ala Phe Lys Leu Arg Ala Trp Phe Asp Ser Glu Gly Gln Val Val
    210                 215                 220

Glu Gly Thr Ser Ile
225

<210> SEQ ID NO 15
<211> LENGTH: 229
<212> TYPE: PRT
<213> ORGANISM: Schizosaccharomyces pombe
<220> FEATURE:
<223> OTHER INFORMATION: RPA70 194-422

<400> SEQUENCE: 15

Ile Arg Ala Arg Val Thr Asn Lys Ser Glu Val Lys His Trp His Asn
  1               5                  10                  15

Gln Arg Gly Glu Gly Lys Leu Phe Ser Val Asn Leu Leu Asp Glu Ser
             20                  25                  30

Gly Glu Ile Arg Ala Thr Gly Phe Asn Asp Gln Val Asp Ala Phe Tyr
```

-continued

```
                35                  40                  45
Lys Ile Leu Gln Glu Gly Ser Val Tyr Tyr Ile Ser Arg Cys Arg Val
         50                  55                  60
Asn Ile Ala Lys Lys Gln Tyr Thr Asn Val Gln Asn Glu Tyr Glu Leu
 65                  70                  75                  80
Met Phe Glu Arg Asp Thr Glu Ile Arg Lys Ala Glu Asp Gln Thr Ala
                 85                  90                  95
Val Pro Val Ala Lys Phe Ser Phe Val Ser Leu Gln Glu Val Gly Asp
                100                 105                 110
Val Ala Lys Asp Ala Val Ile Asp Val Ile Gly Val Leu Gln Asn Val
                115                 120                 125
Gly Pro Val Gln Gln Ile Thr Ser Arg Ala Thr Ser Arg Gly Phe Asp
        130                 135                 140
Lys Arg Asp Ile Thr Ile Val Asp Gln Thr Gly Tyr Glu Met Arg Val
145                 150                 155                 160
Thr Leu Trp Gly Lys Thr Ala Ile Glu Phe Ser Val Ser Glu Glu Ser
                165                 170                 175
Ile Leu Ala Phe Lys Gly Val Lys Val Asn Asp Phe Gln Gly Arg Ser
                180                 185                 190
Leu Ser Met Leu Thr Ser Ser Thr Met Ser Val Asp Pro Asp Ile Gln
        195                 200                 205
Glu Ser His Leu Leu Lys Gly Trp Tyr Asp Gly Gln Gly Arg Gly Gln
210                 215                 220
Glu Phe Ala Lys His
225

<210> SEQ ID NO 16
<211> LENGTH: 228
<212> TYPE: PRT
<213> ORGANISM: Saccharomyces cerevisiae
<220> FEATURE:
<223> OTHER INFORMATION: RPA70 198-426

<400> SEQUENCE: 16

Ile Lys Ala Arg Val Ser Tyr Lys Gly Glu Ile Lys Thr Trp His Asn
 1               5                  10                  15
Gln Arg Gly Asp Gly Lys Leu Phe Asn Val Asn Phe Leu Asp Thr Ser
                20                  25                  30
Gly Glu Ile Arg Ala Thr Ala Phe Asn Asp Phe Ala Thr Lys Phe Asn
         35                  40                  45
Glu Ile Leu Gln Glu Gly Lys Val Tyr Tyr Val Ser Lys Ala Lys Leu
     50                  55                  60
Gln Pro Ala Lys Pro Gln Phe Thr Asn Leu Thr His Pro Tyr Glu Leu
 65                  70                  75                  80
Asn Leu Asp Arg Asp Thr Val Ile Glu Glu Cys Phe Asp Glu Ser Asn
                 85                  90                  95
Val Pro Lys Thr His Phe Asn Phe Ile Lys Leu Asp Ala Ile Gln Asn
                100                 105                 110
Gln Glu Val Asn Ser Asn Val Asp Val Leu Gly Ile Ile Gln Thr Ile
            115                 120                 125
Asn Pro His Phe Glu Leu Thr Ser Arg Ala Gly Lys Lys Phe Asp Arg
        130                 135                 140
Arg Asp Ile Thr Ile Val Asp Asp Ser Gly Phe Ser Ile Ser Val Gly
145                 150                 155                 160
Leu Trp Asn Gln Gln Ala Leu Asp Phe Asn Leu Pro Glu Gly Ser Val
```

```
                    165                 170                 175
Ala Ala Ile Lys Gly Val Arg Val Thr Asp Phe Gly Gly Lys Ser Leu
            180                 185                 190

Ser Met Gly Phe Ser Ser Thr Leu Ile Pro Asn Pro Glu Ile Pro Glu
            195                 200                 205

Ala Tyr Ala Leu Lys Gly Trp Tyr Asp Ser Lys Gly Arg Asn Ala Asn
            210                 215                 220

Phe Ile Thr Leu
225

<210> SEQ ID NO 17
<211> LENGTH: 231
<212> TYPE: PRT
<213> ORGANISM: Crithidia fasciculata
<220> FEATURE:
<223> OTHER INFORMATION: RPA70 25-255

<400> SEQUENCE: 17

Ile Arg Ala Arg Val Ala Asp Lys Ser Asp Ile Arg Thr Trp Asn Lys
 1               5                  10                  15

Pro Thr Ser Gln Gly Lys Leu Phe Ser Phe Thr Leu Ile Asp Glu Ser
            20                  25                  30

Ala Ala Ile Arg Ala Thr Val Phe Asn Asp Ala Val Asp Thr Phe Glu
        35                  40                  45

Pro Leu Val Val Asn Gly Gln Val Tyr Tyr Phe Ser Gly Gly Gln Val
    50                  55                  60

Lys Asn Ala Asn Arg Arg Phe Ser Asn Val Asn Asn Asp Tyr Glu Leu
65                  70                  75                  80

Thr Phe Asp Arg Ala Ser Glu Val Ile Leu Ala Arg Gln Asp Ser Ser
                85                  90                  95

Ala Ala Ala Leu Pro Met Gln Arg Tyr Asn Phe Val Pro Ile Glu Leu
            100                 105                 110

Leu Lys Gln Arg Glu Val Gly Ser Leu Val Asp Val Leu Gly Val Val
        115                 120                 125

Leu Lys Val Asp Glu Ile Ser Ser Ile Thr Gln Lys Ser Thr Gly Arg
    130                 135                 140

Glu Leu Ile Lys Arg Asn Val Lys Ile Gly Asp Met Ser Ala Ala Val
145                 150                 155                 160

Glu Val Thr Phe Trp Asn Asp Glu Ala Lys Ala Trp Asn Tyr Pro Val
                165                 170                 175

Gly Thr Val Val Ala Leu Arg Gln Leu Lys Val Gly Ser Phe Asp Gly
            180                 185                 190

Val Thr Leu Ser Ser Thr Tyr Gln Thr Lys Ile Asp Val Asn Pro Ala
        195                 200                 205

Asp Leu Pro Asp Val Lys Lys Leu Ala Thr Trp Tyr Val Ser Thr Gly
    210                 215                 220

Gly Ala Asn Val Val Ser Leu
225                 230

<210> SEQ ID NO 18
<211> LENGTH: 81
<212> TYPE: PRT
<213> ORGANISM: Escherichia coli
<220> FEATURE:
<223> OTHER INFORMATION: SSB 25-107

<400> SEQUENCE: 18
```

```
Asn Gly Gly Ala Val Ala Asn Ile Thr Leu Ala Thr Ser Glu Ser Trp
  1               5                  10                  15

Arg Asp Lys Ala Thr Gly Glu Met Lys Glu Thr Gln Glu Trp His Arg
                 20                  25                  30

Val Val Leu Phe Gly Lys Leu Ala Glu Val Ala Ser Glu Tyr Lys Gly
             35                  40                  45

Ser Gln Val Tyr Ile Glu Gly Gln Leu Arg Thr Arg Lys Trp Thr Asp
     50                  55                  60

Gln Ser Gly Gln Asp Arg Tyr Thr Thr Glu Val Val Asn Val Gly
 65                  70                  75                  80

Gly

<210> SEQ ID NO 19
<211> LENGTH: 84
<212> TYPE: PRT
<213> ORGANISM: Methanococcus jannaschii
<220> FEATURE:
<223> OTHER INFORMATION: MJ1159 80-163

<400> SEQUENCE: 19

Ile Thr Gly Val Ile Thr Asp Ile Ser Glu Ile Lys Thr Phe Lys Arg
  1               5                  10                  15

Arg Asp Gly Ser Leu Gly Lys Tyr Lys Arg Ile Thr Ile Ala Asp Lys
                 20                  25                  30

Ser Gly Thr Ile Arg Met Thr Leu Trp Asp Asp Leu Ala Glu Leu Asp
             35                  40                  45

Val Lys Val Gly Asp Val Ile Lys Ile Glu Arg Ala Arg Ala Arg Lys
     50                  55                  60

Trp Arg Asn Asn Leu Glu Leu Ser Ser Thr Ser Glu Thr Lys Ile Lys
 65                  70                  75                  80

Lys Leu Glu Asn

<210> SEQ ID NO 20
<211> LENGTH: 84
<212> TYPE: PRT
<213> ORGANISM: Methanococcus jannaschii
<220> FEATURE:
<223> OTHER INFORMATION: MJ1159 188-271

<400> SEQUENCE: 20

Phe Glu Gly Glu Val Ile Ser Ala Leu Pro Ile Lys Glu Phe Lys Arg
  1               5                  10                  15

Ala Asp Gly Ser Ile Gly Lys Leu Lys Ser Phe Ile Val Arg Asp Glu
                 20                  25                  30

Thr Gly Ser Ile Arg Val Thr Leu Trp Asp Asn Leu Thr Asp Ile Asp
             35                  40                  45

Val Gly Arg Gly Asp Tyr Val Arg Val Arg Gly Tyr Ile Arg Glu Gly
     50                  55                  60

Tyr Tyr Gly Gly Leu Glu Cys Thr Ala Asn Tyr Val Glu Ile Leu Lys
 65                  70                  75                  80

Lys Gly Glu Lys

<210> SEQ ID NO 21
<211> LENGTH: 90
<212> TYPE: PRT
<213> ORGANISM: Methanococcus jannaschii
<220> FEATURE:
<223> OTHER INFORMATION: MJ1159 293-382
```

-continued

<400> SEQUENCE: 21

Val Lys Gly Arg Val Ile Ala Ile Ser Asn Lys Lys Ser Val Asp Leu
1               5                   10                  15

Asp Gly Glu Ile Ala Lys Val Gln Asp Ile Ile Leu Asp Asn Gly Thr
            20                  25                  30

Gly Arg Val Arg Val Ser Phe Trp Arg Gly Lys Thr Ala Leu Leu Glu
        35                  40                  45

Asn Ile Lys Glu Gly Asp Leu Val Arg Ile Thr Asn Cys Arg Val Lys
    50                  55                  60

Thr Phe Tyr Asp Arg Glu Gly Asn Lys Arg Thr Asp Leu Val Ala Thr
65                  70                  75                  80

Leu Glu Thr Glu Val Ile Lys Asp Glu Asn
                85                  90

<210> SEQ ID NO 22
<211> LENGTH: 84
<212> TYPE: PRT
<213> ORGANISM: Methanococcus jannaschii
<220> FEATURE:
<223> OTHER INFORMATION: MJ1159 411-493

<400> SEQUENCE: 22

Met Ile Ala Gln Val Val Glu Asp Tyr Gly Val Asn Glu Ile Glu Phe
1               5                   10                  15

Glu Asp Lys Val Arg Lys Val Arg Asn Leu Leu Leu Glu Asp Gly Thr
            20                  25                  30

Gly Arg Ile Arg Leu Ser Leu Trp Asp Asp Leu Ala Glu Ile Glu Ile
        35                  40                  45

Lys Glu Gly Asp Ile Val Glu Ile Leu His Ala Tyr Ala Lys Glu Arg
    50                  55                  60

Gly Asp Tyr Ile Asp Leu Val Ile Gly Lys Tyr Gly Arg Ile Ile Ile
65                  70                  75                  80

Asn Pro Glu Gly

<210> SEQ ID NO 23
<211> LENGTH: 92
<212> TYPE: PRT
<213> ORGANISM: Artificial Sequence
<220> FEATURE:
<223> OTHER INFORMATION: Description of Artificial Sequence:consensus
      sequence derived from four MJ1159 putative
      ssDNA-binding domains
<220> FEATURE:
<221> NAME/KEY: MOD_RES
<222> LOCATION: (1)..(92)
<223> OTHER INFORMATION: Xaa = any amino acid

<400> SEQUENCE: 23

Xaa Xaa Gly Xaa Val Ile Xaa Ile Ser Xaa Ile Lys Thr Phe Lys Arg
1               5                   10                  15

Xaa Asp Gly Ser Ile Gly Lys Val Lys Xaa Ile Ile Leu Xaa Asp Gly
            20                  25                  30

Thr Gly Arg Ile Arg Val Thr Leu Trp Asp Asp Leu Ala Glu Ile Xaa
        35                  40                  45

Xaa Asp Ile Lys Glu Gly Asp Xaa Val Arg Ile Xaa Xaa Ala Arg Ala
    50                  55                  60

Xaa Xaa Xaa Xaa Xaa Arg Glu Tyr Xaa Xaa Xaa Leu Glu Leu Val Ala
65                  70                  75                  80

Thr Xaa Glu Thr Xaa Ile Lys Lys Xaa Xaa Glu Asn

```
<210> SEQ ID NO 24
<211> LENGTH: 93
<212> TYPE: PRT
<213> ORGANISM: Artificial Sequence
<220> FEATURE:
<223> OTHER INFORMATION: Description of Artificial Sequence:eukaryotic
      ssDNA-binding domain consensus
<220> FEATURE:
<221> NAME/KEY: MOD_RES
<222> LOCATION: (1)..(93)
<223> OTHER INFORMATION: Xaa = any amino acid

<400> SEQUENCE: 24

Ile Lys Ala Arg Val Thr Asn Lys Ser Glu Ile Arg Thr Trp Ser Asn
1               5                   10                  15

Xaa Arg Gly Glu Gly Lys Leu Phe Ser Xaa Xaa Leu Xaa Asp Glu Ser
            20                  25                  30

Gly Glu Ile Arg Ala Thr Ala Phe Asn Asp Gln Xaa Asp Lys Phe Xaa
        35                  40                  45

Asp Ile Ile Gln Val Gly Lys Val Tyr Tyr Phe Ser Lys Gly Xaa Leu
    50                  55                  60

Lys Ile Ala Asn Lys Gln Tyr Thr Asn Val Asn Asp Tyr Xaa Glu Leu
65                  70                  75                  80

Thr Phe Xaa Arg Glu Thr Xaa Val Xaa Xaa Cys Glu Asp
                85                  90

<210> SEQ ID NO 25
<211> LENGTH: 72
<212> TYPE: PRT
<213> ORGANISM: Methanococcus jannaschii
<220> FEATURE:
<223> OTHER INFORMATION: MJ1159 524-595

<400> SEQUENCE: 25

Asp Thr Leu Phe Leu Tyr Leu Cys Pro Asn Cys Arg Lys Arg Val Val
1               5                   10                  15

Glu Ile Asp Gly Ile Tyr Asn Cys Pro Ile Cys Gly Asp Val Glu Pro
            20                  25                  30

Glu Glu Ile Leu Arg Leu Asn Phe Val Val Asp Asp Gly Thr Gly Thr
        35                  40                  45

Leu Leu Cys Arg Ala Tyr Asp Arg Arg Val Glu Lys Met Leu Lys Met
    50                  55                  60

Asn Arg Glu Glu Leu Lys Asn Leu
65                  70

<210> SEQ ID NO 26
<211> LENGTH: 77
<212> TYPE: PRT
<213> ORGANISM: Drosophila melanogaster
<220> FEATURE:
<223> OTHER INFORMATION: RPA70 457-533 zinc-finger domain

<400> SEQUENCE: 26

Glu Asn Ala Phe Tyr Arg Ala Cys Pro Gln Ser Asp Cys Asn Lys Lys
1               5                   10                  15
```

```
Val Val Asp Glu Gly Asn Asp Gln Phe Arg Cys Glu Lys Cys Asn Ala
         20                  25                  30

Leu Phe Pro Asn Phe Lys Tyr Arg Leu Leu Ile Asn Met Ser Ile Gly
         35                  40                  45

Asp Trp Thr Ser Asn Arg Trp Val Ser Ser Phe Asn Glu Val Gly Glu
         50                  55                  60

Gln Leu Leu Gly His Thr Ser Gln Glu Val Gly Glu Ala
 65                  70                  75

<210> SEQ ID NO 27
<211> LENGTH: 77
<212> TYPE: PRT
<213> ORGANISM: Homo sapiens
<220> FEATURE:
<223> OTHER INFORMATION: RPA70 474-550 zinc-finger domain

<400> SEQUENCE: 27

Glu Asn Cys Met Tyr Gln Ala Cys Pro Thr Gln Asp Cys Asn Lys Lys
  1               5                  10                  15

Val Ile Asp Gln Gln Asn Gly Leu Tyr Arg Cys Glu Lys Cys Asp Thr
         20                  25                  30

Glu Phe Pro Asn Phe Lys Tyr Arg Met Ile Leu Ser Val Asn Ile Ala
         35                  40                  45

Asp Phe Gln Glu Asn Gln Trp Val Thr Cys Phe Gln Glu Ser Ala Glu
         50                  55                  60

Ala Ile Leu Gly Gln Asn Ala Ala Tyr Leu Gly Glu Leu
 65                  70                  75

<210> SEQ ID NO 28
<211> LENGTH: 77
<212> TYPE: PRT
<213> ORGANISM: Xenopus laevis
<220> FEATURE:
<223> OTHER INFORMATION: RPA70 465-541 zinc-finger domain

<400> SEQUENCE: 28

Glu Asn Cys Leu Tyr Gln Ala Cys Pro Ser Gln Asp Cys Asn Lys Lys
  1               5                  10                  15

Val Ile Asp Gln Gln Asn Gly Leu Phe Arg Cys Glu Lys Cys Asn Lys
         20                  25                  30

Glu Phe Pro Asn Phe Lys Tyr Arg Leu Ile Leu Ser Ala Asn Ile Ala
         35                  40                  45

Asp Phe Gly Glu Asn Gln Trp Ile Thr Cys Phe Gln Glu Ser Ala Glu
         50                  55                  60

Ser Ile Leu Gly Gln Asn Ala Thr Tyr Leu Gly Glu Leu
 65                  70                  75

<210> SEQ ID NO 29
<211> LENGTH: 76
<212> TYPE: PRT
<213> ORGANISM: Schizosaccharomyces pombe
<220> FEATURE:
<223> OTHER INFORMATION: RPA70 470-545 zinc-finger domain

<400> SEQUENCE: 29

Lys Asn Val Ser Tyr Pro Ala Cys Pro Ala Ala Asp Cys Asn Lys Lys
  1               5                  10                  15
```

-continued

```
Val Phe Asp Gln Gly Gly Ser Trp Arg Cys Glu Lys Cys Asn Lys Glu
                20                  25                  30
Tyr Asp Ala Pro Gln Tyr Arg Tyr Ile Ile Thr Ile Ala Val Gly Asp
            35                  40                  45
His Thr Gly Gln Leu Trp Leu Asn Val Phe Asp Val Gly Lys Leu
    50                  55                  60
Ile Met His Lys Thr Ala Asp Glu Leu Asn Asp Leu
65                  70                  75
```

<210> SEQ ID NO 30
<211> LENGTH: 77
<212> TYPE: PRT
<213> ORGANISM: Saccharomyces cerevisiae
<220> FEATURE:
<223> OTHER INFORMATION: RPA70 479-555 zinc-finger domain

<400> SEQUENCE: 30

```
Asp Asn Phe Ala Tyr Pro Ala Cys Ser Asn Glu Asn Cys Asn Lys Lys
1               5                   10                  15
Val Leu Glu Gln Pro Asp Gly Thr Trp Arg Cys Glu Lys Cys Asp Thr
                20                  25                  30
Asn Asn Ala Arg Pro Asn Trp Arg Tyr Ile Leu Thr Ile Ser Ile Ile
            35                  40                  45
Asp Glu Thr Asn Gln Leu Trp Leu Thr Leu Phe Asp Asp Gln Ala Lys
    50                  55                  60
Gln Leu Leu Gly Val Asp Ala Asn Thr Leu Met Ser Leu
65                  70                  75
```

<210> SEQ ID NO 31
<211> LENGTH: 76
<212> TYPE: PRT
<213> ORGANISM: Crithidia fasciculata
<220> FEATURE:
<223> OTHER INFORMATION: RPA70 306-381 zinc-finger domain

<400> SEQUENCE: 31

```
Asp Ala Gln Trp Tyr Asp Ala Cys Pro Thr Cys Asn Lys Lys Val Thr
1               5                   10                  15
Glu Glu Gly Ala Gln Gly Asp Arg Phe Arg Cys Glu Lys Cys Asp Ala
                20                  25                  30
Thr Val Val Pro Thr Gln Arg Tyr Leu Val Ser Ile Gln Val Thr Asp
            35                  40                  45
Asn Val Ser Gln Val Trp Leu Thr Leu Phe Asn Glu Ala Gly Val Glu
    50                  55                  60
Phe Phe Gly Met Glu Ala Ser Glu Leu Lys Arg Arg
65                  70                  75
```

SINGLE STRANDED DNA BINDING PROTEINS FROM ARCHAEA AND USES THEREFOR

CROSS REFERENCE TO RELATED APPLICATIONS

This application is a continuation of U.S. patent application Ser. No. 09/631,616, filed Aug. 4, 2000, now U.S. Pat. No. 6,852,832, which claims priority to U.S. Provisional Application No. 60/147,680, filed Aug. 6, 1999, both of which are hereby incorporated by reference.

STATEMENT REGARDING FEDERALLY SPONSORED RESEARCH

This invention was made with government support under grant number AI-18987 awarded by the National Institutes of Health. The government has certain rights in the invention.

BACKGROUND OF THE INVENTION

Single stranded (ss) DNA-binding proteins are essential to virtually all aspects of DNA metabolism. These proteins, typified by the *Escherichia coli* ssDNA-binding protein (SSB) in Bacteria (Sancar, A., et al., *Proc. Natl. Acad. Sci. USA* 78, 4274-4278 (1981), Lohman, T. M. et al, *Annu. Rev. Biochem.* 63, 527-570 (1994)) and the human replication protein-A (RPA) complex in Eucarya (Fairman, M. P. et al., *Embo J.* 7, 1211-1218 (1988); Wold, M. S. et al., *Proc. Natl. Acad. Sci. USA* 85, 2523-2527 (1988); and Wold, M. S., *Annu. Rev. Biochem.* 66, 61-92 (1997)), are required for in vitro DNA replication and are key components in DNA recombination and repair. Although functionally equivalent, SSB protein and RPA have very different protein structures. Bacterial SSB proteins are encoded by a single gene, although the active form is a homotetramer of SSB where each monomer contributes one ssDNA-binding domain. By contrast, the RPA complex is composed of three distinct subunits.

The large subunit of RPA, RPA70, has several-domains, each associated with a given function (Gomes, X. V., *J. Biol. Chem.* 270, 4534-4543 (1995), Gomes, X. V. *Biochemistry* 35, 10558-10568 (1996)). The N-terminal region of RPA70 mediates interactions between RPA and many cellular or viral proteins, whereas the central region contains two functional, homologous, ssDNA-binding sites that are arranged in tandem. The C-terminal region of RPA70 is involved in the assembly of the heterotrimeric complex. The intermediate subunit of RPA, RPA32, which carries a third functional ssDNA-binding site (Bochkareva, E., et al., *J. Biol. Chem.* 273, 3932-3947 (1998)), is phosphorylated in a cell-cycle dependent manner, although no specific role is attributed to this modification (Henricksen, L. A., *Nucleic Acids Res.* 24, 3107-3112 (1996)). Finally, the small subunit (RPA14) carries an additional putative ssDNA-binding motif; however, but no direct evidence for DNA binding by this subunit exists.

Interestingly, the four ssDNA-binding motifs of RPA and the motif of SSB protein show a significant degree of homology (Philipova, D. et al., *Genes Dev.* 10, 2222-2233 (1996)). Moreover, there is striking structural conservation among the ssDNA-binding domains of RPA, and members of both the prokaryotic SSB protein family and the phage-encoded SSB proteins (Bochkarev, A., *Nature* 385, 176-181 (1997)). These findings suggest that RPA and SSB protein originated from a common ancestral ssDNA-binding protein and then diverged through evolution by a combination of duplications, deletions, and additions.

While ssDNA binding proteins have been known for Bacteria and for Eucarya, the art has not identified a counterpart of a ssDNA binding protein for the third domain of life, the Archaea.

SUMMARY OF THE INVENTION

We have discovered a novel type of ssDNA-binding protein in the genomes of several archaeons. These proteins possess four conserved DNA binding sites within a single polypeptide or, in one case, two polypeptides. Because members of the Archaea exist in extreme conditions of pH, salt concentrations, and low and high temperatures, the ssDNA binding proteins of these archaeons are especially robust reagents for use in biotechnical applications involving DNA, such as PCR.

The invention provides isolated nucleic acid sequences encoding an ssDNA-binding protein from an Archaeon. In particular, the Archaeon is selected from the group consisting of *Methanococcus jannaschii, Methanobacter theromoautotrophicum*, and *Archaeoglobus fulgidus*. The nucleic acid sequence can have, for example, 70% or more sequence identity to a nucleic acid selected from the group consisting of SEQ ID NO:2, SEQ ID NO:3, SEQ ID NO:4, SEQ ID NO:7, and SEQ ID NO:8, or can be selected from the group consisting of SEQ ID NO:2, SEQ ID NO:3, SEQ ID NO:4, SEQ ID NO:7, and SEQ ID NO:8.

The invention further provides recombinant expression vectors containing any of the nucleic acid sequences described above, as well as cells containing one or more of these recombinant expression vectors. In some preferred embodiments, the recombinant expression vectors are in *E. coli* cells.

Additionally, the invention provides isolated ssDNA-binding proteins. In particular, the invention provides an isolated ssDNA-binding protein wherein the ssDNA-binding protein is isolated from an Archaeon selected from the group consisting of *Methanococcus jannaschii, Methanobacter theromoautotrophicum*, and *Archaeoglobus fulgidus*. The ssDNA-binding protein can have 70% or more sequence identity to an amino acid sequence selected from the group consisting of SEQ ID NOS:1, 5, 6, 9, and 10, or can be selected from the group consisting of SEQ ID NOS:1, 5, 6, 9, and 10.

The invention further provides a method of performing polymerase chain reaction, comprising using a ssDNA-binding protein isolated from an archaeon. The method can conveniently be performed using an ssDNA-binding protein of an archaeon selected from the group consisting of *Methanococcus jannaschii, Methanobacter theromoautotrophicum*, and *Archaeoglobus fulgidus*. In particular, the method can use ssDNA binding proteins having 70% or more sequence identity to an amino acid sequence selected from the group consisting of SEQ ID NOS:1, 5, 6, 9, and 10, or can be selected from the group consisting of SEQ ID NOS:1, 5, 6, 9, and 10

The sequence numbering relates to MJ1159. All alignments and consensus building were performed using the Multalin version 5.3.3 program (available on the internet by entering "http://www." followed by "toulouse.inra.fr/multalin.html") and the Wisconsin Package Version 9.1 (Genetics Computer Group (GCG), Madison, Wis.). B. Alignment of the four putative ssDNA-binding domains in MJ1159 (SEQ ID NO:19-22). The fonts are as in A.; additional conservative substitutions between two binding domains are underlined. Dashes represent gaps in the alignment. C. The consensus sequence derived from the four MJ1159 domains is shown (SEQ ID NO:23), as is a eukaryotic ssDNA-binding domain A consensus (SEQ ID NO:24) derived from the sequences shown in A. Upper case indicates highly conserved residues, lower case indicates less conserved residues; asterisks indicate a lack of consensus. Two dots between the consensus sequences indicate identical residues; one dot indicates conserved substitutions. Three residues were omitted from the eukaryotic consensus in order to allow a better alignment; these are shown below the alignment. Cf, *Crithidia fasciculata*; Dm, *Drosophila melanogaster*; Hs, *Homo sapiens*; Sp, *Schizosaccharomyces pombe*; Sc, *Saccharomyces cerevisiae*; Xl, *Xenopus laevis*.

Figure 2:
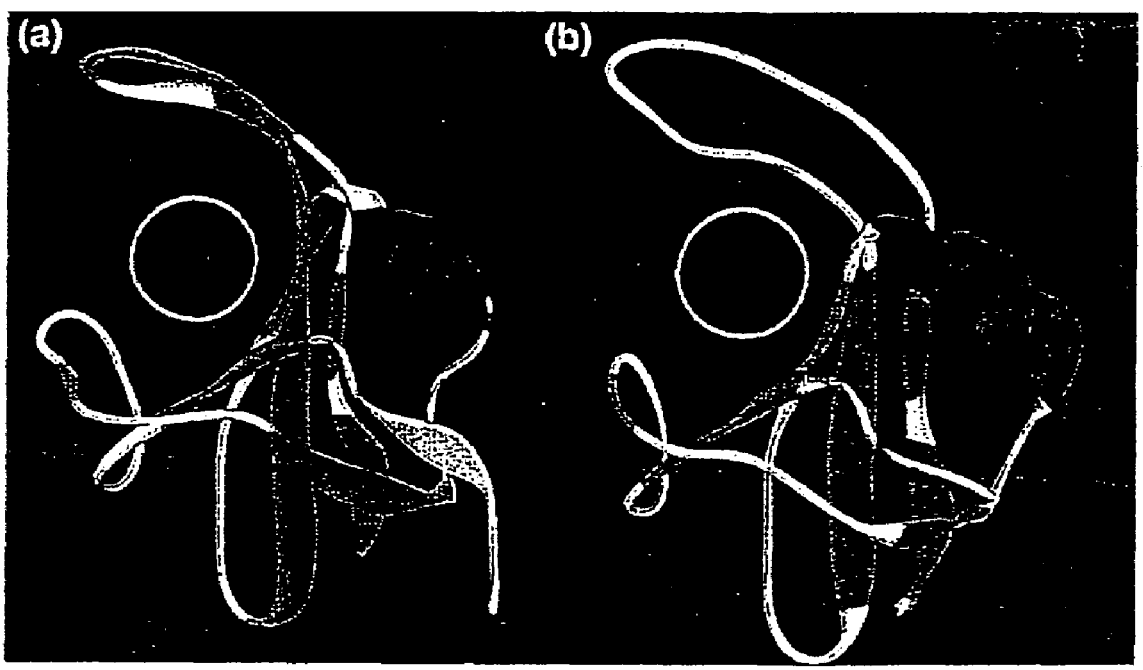

FIG. 2: Structure of the ssDNA-binding domain A. A. Human RPA70 ssDNA-binding domain A. B. *Methanococcus jannaschii* MJ1159 ssDNA-binding domain A (residues 80-162) modeled using the structure of human RPA70 domain A as a guide. The modeling was carried out by the Swiss model server using the ProModII and Gromos96 programs (available on the internet by entering "http://www." followed by "expasy.ch/swissmod/SWISS-MODEL.html") for comparative protein modeling and energy minimization, respectively. The structures are shown so that the axis of the channel in which DNA binds is perpendicular to the figure (the position of DNA is shown as a circle).

FIG. 3: Alignment of the zinc-finger domains of eukaryotic RPA70s (SEQ ID NO:26-31) and residues 524-595 of MJ1159 (SEQ ID NO:25). Conserved residues are shown in bold; conservative substitutions are shown in italics. Cysteine residues thought to be part of a zinc-finger domain are indicated by asterisks. Abbreviations: Cf, *Crithidia fasciculata*; Dm, *Drosophila melanogaster*; Hs, *Homo sapiens*; Sp, *Schizosaccharomyces pombe*; Sc, *Saccharomyces cerevisiae*; Xl, *Xenopus laevis*.

Figure 4:
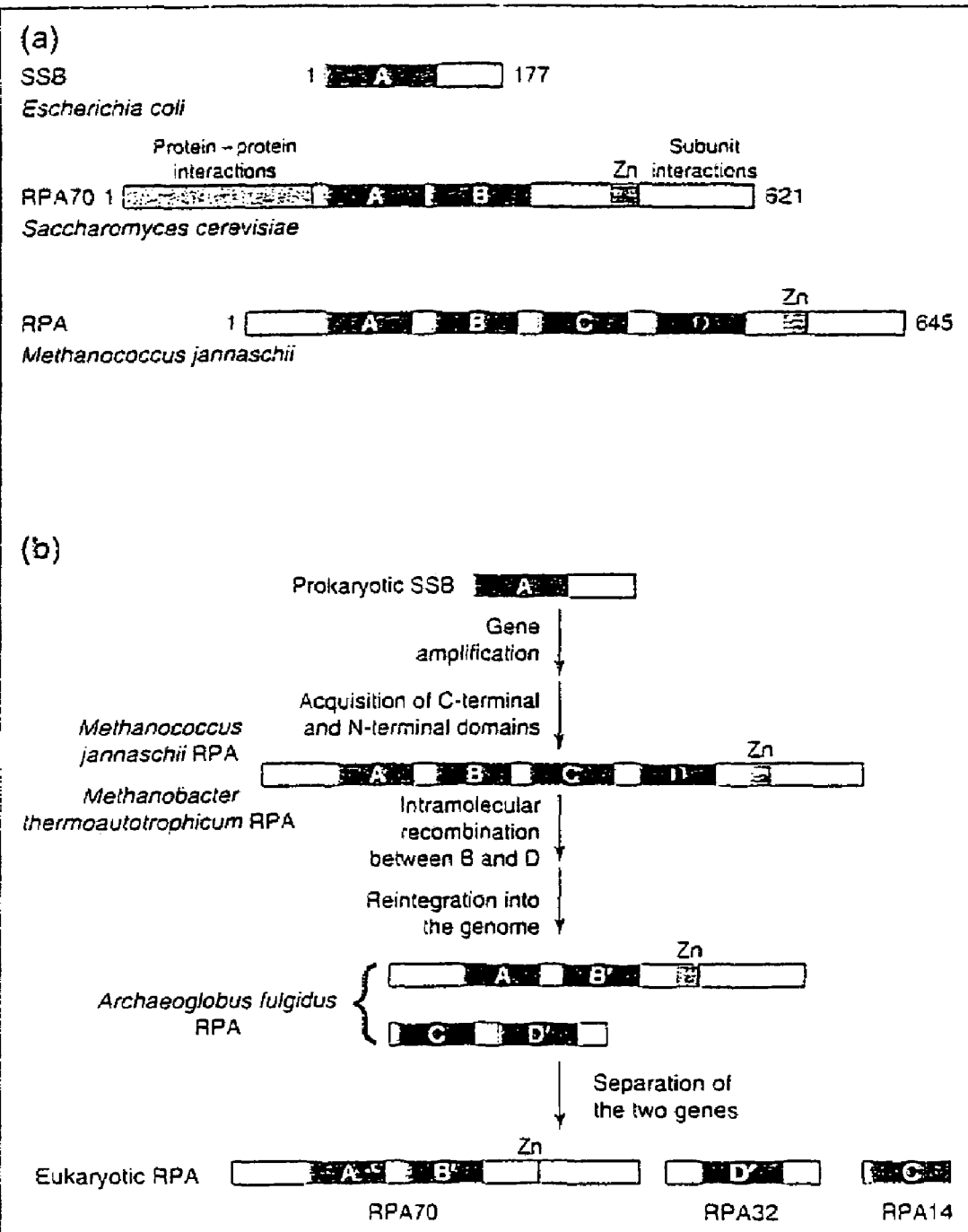

FIG. 4: A. Comparison of the structures of ssDNA-binding proteins in Bacteria, Eukarya and Archaea. The ssDNA-binding domains are indicated by letters, putative zinc-finger domains are indicated by the letters "Zn" over the domain, the protein-protein interaction domain is indicated by text over the domain. B. Model for the evolution of ssDNA-binding proteins. B' and D' indicate products of homologous recombination. RPA, replication protein A; SSB, prokaryotic ssDNA-binding protein. Indications for the ssDNA-binding domains and zinc finger domains are as for FIG. 4A.

DETAILED DESCRIPTION

I. Uses of the ssDNA-Binding Proteins of the Invention

Members of the Archaea typically live in conditions of extreme heat, pH, or salt concentrations. Thus, they offer a source of enzymes which can be useful reagents in assays and other commercial reactions. We have identified nucleic acid sequences encoding ssDNA-binding proteins in the archaeons *Methanococcus jannaschii*, *Methanobacter thermoautotrophicum* and *Archaeoglobus fulgidus*. All three organisms are thermophiles, and their DNA replication accordingly takes place at high temperature. *M. jannaschii*, for example, grows near deep ocean thermal vents under conditions of 200 atm and a temperature range of 48° to 94° C. (see, e.g., Bult, C. J. et al., Science 273: 1058-1073 (1996)). The ssDNA-binding proteins of these organisms are therefore robust reagents useful for a variety of biotechnical applications. For example, the proteins are especially useful in applications in which functioning under high temperature conditions is desirable, such as the temperatures usually associated with the polymerase chain reaction (PCR).

ssDNA-binding proteins are known to be involved in eliminating DNA secondary structure, and in DNA recombination. The ssDNA-binding proteins of the invention are therefore useful reagents for genetic engineering and other procedures involving DNA recombination, as well as in performing PCR.

During PCR, the activity of ssDNA-binding proteins in eliminating secondary structure permits DNA polymerase to replicate more of the DNA template strand in each PCR cycle than would be replicated in the absence of the protein, thereby increasing yield. Moreover, temperature-resistant ssDNA-binding proteins are not inactivated by the temperature cycling which is part of the PCR process, and thus do not have to be replaced before the next reaction can proceed. This enhances the ability to automate the procedures. Thus, use of heat-resistant ssDNA-binding proteins, like the ones provided here, not only increases the yield of each PCR cycle, but also permits automation of the overall process and the speed with which cycles can be conducted.

PCR reactions generally benefit from the use of between about. 0.05 µg to about 1 µg of ssDNA-binding protein of the invention. Higher yields of PCR product have been obtained, for example, by using 0.2 to 0.6 µg of *M. jannaschii* ssDNA-binding protein in a 50 µL PCR reaction containing 1 unit of Taq polymerase and 50 µg of DNA. Using these amounts as guidelines, persons of skill in the art can readily determine and optimize the amounts to use for any given volume of PCR reactants or amount of DNA. Accordingly, among other advantages, the invention has significant benefits in the practice of PCR.

II. Discovery of the ssDNA-Binding Protein of *Methanococcus jannaschii*

A. Search for the Gene

In a major feat, which made the cover of Science, the genome of an entire autotrophic archaeon, *Methanococcus jannaschii*, was sequenced in 1996. (Bult, C. J. et al., Science 273: 1058-1073 (1996)). According to the news article accompanying the research report, the study's forty co-authors searched the existing databases of bacterial and eukaryotic genomes for homologs. Morell, V., Science, 273: 1043-1045 (1996). The team found matches for only 44% of the genes, id., and only 38% of the genes could be assigned a putative cellular role with any confidence. Bult, et al., supra. The majority of the genes could not be identified.

We have now been able to identify the function of one of the genes to which Bult et al. could not assign a function. Briefly, we searched the *M. jannaschii* genome for a protein with homology to the *Saccharomyces cerevisiae* RFA1 gene, which encodes the RPA70 subunit, using the Grasta program (available on the internet by entering "http://www." followed by "tigr.org") and a low cutoff score. Several putative candidates were retrieved and were subsequently used as queries in Blast or PSI-Blast searches (on the internet by entering "http://www." followed by "ncbi.nlm.nih.gov"). One of these *M. jannaschii* sequences, ORF MJ1159, retrieved the *Crithidia fasciculata* RFA1 gene product. The MJ1159 protein (SEQ ID NO:1) is 645 amino acids in length and, interestingly, one of the regions of similarity detected by Blast corresponds to the ssDNA-binding domain A of *C. fascicu-*

*lata* RPA70. MJ1159 is one of the genes for which Bult et al. could not determine a function. The entire sequence of the protein is publicly available, and can be accessed on the Internet at the National Center for Biotechnology Information ("NCBI") website (on the internet at "www." followed by "ncbi.nlm.nih.gov"). It can be found using the NCBI's Entrez browser under accession number F64444. The gene sequence (SEQ ID NO:2) is available at the website of The Institute for Genomic Research (TIGR) (found by entering "www." followed by "tigr.org"), in the microbial database, and can be searched simply by entering MJ1159 in the locus search once one is in the *M. jannaschii* section of the database.

Figure 1:
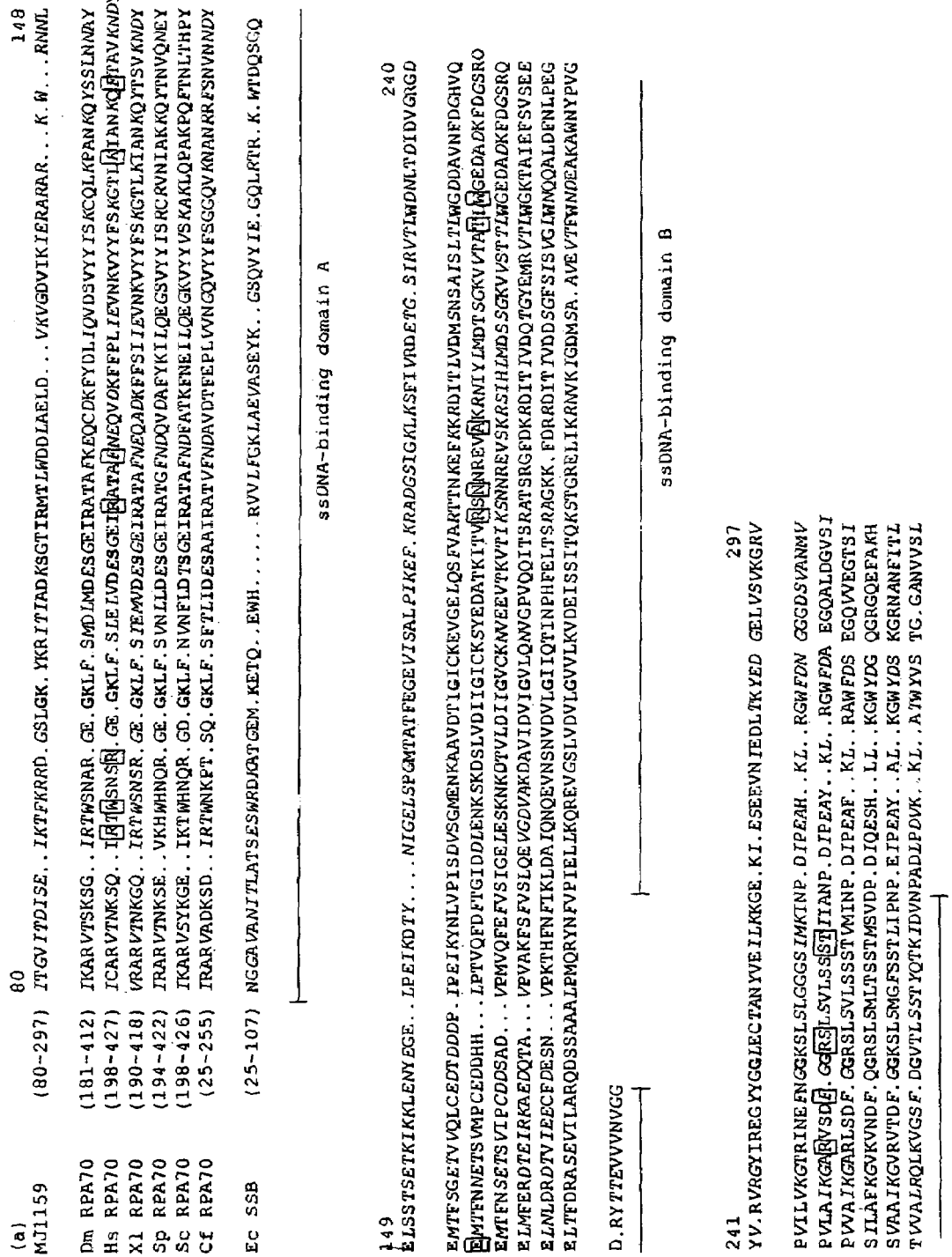
FIG. 1: A. Alignment of residues 80 to 297 of MJ1159 (SEQ ID NO:11) with the RPA70 subunit of a variety of eukaryotes (SEQ ID NOS:12-17) and the *Escherichia coli* (Ec) ssDNA-binding protein (SSB) (SEQ ID NO:18). Residues that are conserved between MJ1159 and its RPA70 counterparts are shown in bold font; conservative substitutions are shown in italics. The corresponding residues in SSB protein are also indicated. Dots represent gaps in the alignment. The boxed residues in human RPA70 are known to contact DNA (Bochkarev, A., *Nature* 385, 176-181 (1997)).

To extend the analysis, we performed multiple alignments of the MJ1159 sequence with sequences of known members of the RPA70 family (FIG. 1A). Residues 80-297 of MJ1159 display a significant degree of similarity to the residues encompassing ssDNA-binding domains A and B of RPA70 from a variety of organisms: this similarity ranged from 39.4% (for residues comprising the domain A of RPA70 from *S. cerevisiae*) to 48.6% (for residues comprising domain A of human RPA70). Therefore, it appears that MJ1159 has two homologous ssDNA-binding domains, named A and B (by analogy with RPA70), which are arranged in tandem.

Interestingly, most of the amino acids that contact DNA in the human RPA70 subunit (boxed residues in FIG. 1A) are conserved in MJ1159: in ssDNA-binding domain A, which makes most of the contacts with DNA (Bochkarev, A., *Nature* 385, 176-181 (1997)), all but one of the DNA-contacting residues are conserved. Homology-dependent structure modeling [which has a high degree of success in predicting the structure of OB-fold family members (A. Edwards, personal communication)] of the archaeal ssDNA-binding domain A (residues 80 to 162) indicates that it shows striking similarity to the equivalent human RPA70 domain (FIG. 2). Both the observed and predicted structures form a channel in which DNA binds, and the residues known to interact with DNA are found along the surface of this channel.

In addition to the homology identified in ssDNA-binding domains A and B, a second region of homology was detected by Blast searches. This region corresponds to residues 400-595 of MJ1159 and shares 29.3 and 35.4% similarity with the C-terminal region of the RPA70 proteins of *C. fasciculata* and *S. cerevisiae*, respectively. Furthermore, a strongly conserved zinc-finger domain, which was recently shown to be important for RPA function (Lin, Y.-L. et al., *J. Biol. Chem.* 273, 1453-1461 (1996)), is located within this region. The four cysteine residues (marked by asterisks in FIG. 3) of this putative zinc-finger are strictly conserved and correctly spaced. The sequences that border this domain also share a significant degree of similarity.

Portions of the discussion herein were published by us in Chedin et al., TIBS 23: 273-277 (1998), which is hereby incorporated by reference.

B. Structure of the Gene

Unexpectedly, alignment of either of the MJ1159 ssDNA-binding domain identified (A or B) with the entire MJ1159 open reading frame revealed two additional homologous regions (called C and D) were revealed. Pairwise comparisons showed that the degree of sequence similarity shared by the four domains ranges from 46% (C-D) to 53% (A-B). When we compared a consensus derived by aligning these four domains with one obtained by aligning the ssDNA-binding domains A of several RPA70 subunits, we found that many residues are conserved between the *M. jannaschii* MJ1159 protein and eukaryotic RPA70 subunits (FIG. 1B). Because the RPA70 ssDNA-binding domain A also shows similarity to *E. coli* SSB protein (Philipova, D. et al., *Genes Dev.* 10, 2222-2233 (1996)) (FIG. 1A), we conclude that Archaea, Bacteria and Eucarya share a common ssDNA-binding motif. The architecture of the archaeal protein—specifically, its four ssDNA-binding motifs and the zinc-finger domain—, is particularly striking, however, and invites speculation about the evolution of ssDNA-binding proteins.

*E. coli* SSB protein binds to DNA as a homotetramer and each monomer contains one DNA-binding motif. Our analysis shows that the protein identified in *M. jannaschii* possesses four conserved putative DNA-binding domains, but that these are present in a single polypeptide chain. This finding might imply that the archaeal RPA functions as a single subunit that does not require multimerization, or, as is the case in eukaryotic RPA, association with other subunits. The fact that searches of the *M. jannaschii* genome using either the middle or small subunits of the eukaryotic RPA did not retrieve any genes that shared significant homology with these proteins supports this hypothesis. However, as elaborated below, the genome of another archaeon reveals a different genetic structure.

C. Discovery of Two Additional Archeaon ssDNA-Binding Proteins

The genome sequences of two archaeons, *Methanobacter thermoautotrophicum* and *Archaeoglobus fulgidus*, were recently released (Klenk, H. P. et al., *Nature* 390, 364-370 (1996), Shamoo, Y. et al., Nature 376, 362-366 (1996)). This allowed us to determine whether or not the findings reported here for *M. jannaschii* hold true for other members of the Archaea. We searched the *M. thermoautotrophicum* genome using MJ1159 as a query and retrieved a 622-residue protein that shares substantial homology with MJ1159 (44% similarity over 410 residues). This protein, MTH1385, also possesses four putative DNA-binding motifs that are arranged in tandem but lacks the zinc-finger domain. However, a second, partially overlapping, gene, MTH1384, lies downstream of MTH1385. The former encodes a protein that shares homology with the C-terminus of MJ1159 and that contains a region that is homologous to the zinc-finger motif described above. It appears that a frameshift was introduced during the sequence and therefore erroneously suggested the existence of two distinct genes—a possibility that was in fact raised by the authors (Klenk, H. P. et al., *Nature* 390, 364-370 (1996)). Thus, it appears that the nucleic acid sequence originally identified as two genes, MTH1384 and MTH1385, actually constitute one continuous gene, and the organization we have described for *M. jannaschii* MJ1159 therefore holds true for a protein in a second archaeon.

The nucleotide sequences of MT1384 and MT1385 are set forth as SEQ ID NOS:3 and 4, respectively. The amino acid sequences of MT1384 and MT1385 are set forth as SEQ ID NOS: 5 and 6, respectively. Given this information, a person of skill in the art has all the information necessary to compare the two sequences, determine the frameshift error, if present, and determine the sequence of the gene and the sequence of the protein it encodes.

In *A. fulgidus*, our initial search identified a gene encoding a 236-residue protein, AF0382, that shares homology with the N-terminus of MJ1159 (46.6% similarity over 236 residues) and contains two DNA-binding domains. Interestingly, a second search revealed a gene encoding a 312-residue protein, AF0780, that shares homology with the C-terminus of MJ1159 (40% similarity over 312 residues) and contains two DNA-binding domains, in addition to the putative zinc-finger region. However, the first AF0780 DNA-binding domain appears to be shorter than a typical ssDNA-binding domain (as defined in FIG. 1A) and only three cysteine residues (compared to the four that are found typically) are present in the zinc-finger region. Thus, it appears that the *A. fulgidus* ssDNA-binding protein is split into two pieces. The nucleotide sequences of AF0382 and AF0780 are set forth as SEQ ID NOS:7 and 8, respectively. The amino acid sequences of AF0382 and AF0780 are set forth as SEQ ID NOS:9 and 10, respectively.

Thus, identifying the function of the *M. jannaschii* MJ1159 gene has permitted us to identify the function of genes from two other archaeons. It is expected that persons of skill in the art will now be able to examine the genome of other archaeons as they are sequenced, find their ssDNA-binding proteins by virtue of their homology to these genes and by virtue of the similarity of their structure to the genes taught herein. It is expected that such comparisons can be readily made for other members of the same genuses, families and orders, as the three archaeons discussed herein, and very likely for other archaeons as well. Finally, the function of the genes can then be confirmed by expressing the encoded proteins and testing them by well known assays for their function as ssDNA-binding proteins.

As noted, the nucleic acid sequences for the ssDNA binding protein genes from *M. thermoautotrophicum* and *A. fulgidus* and the amino acid sequences of the proteins themselves are set forth in the sequence listing. This information is also available in publicly accessible databases. The nucleic acid sequences of the genes encoding the *A. fulgidus* proteins are available on the TIGR website in the microbial database under the name of the organism, at locus search AF0780 and AF0382. The amino acid sequence of the *M thermoautotrophicum* protein is available on the internet by entering "www." followed by "genomecorp.com/genesequences/ methanobacter/abstract.html" (which can be reached by hyperlink from the microbial database of the TIGR website); the gene sequences for both MTH1385 and MTH1384 can be also found in GenBank at locus AE000901.

D. Modifications of the Genes and of the ssDNA-Binding Proteins.

1. Definitions

As used herein, the term "ssDNA-binding protein" means an archaeon protein which binds single-stranded DNA, or a protein with 70% or more sequence identity to one of the exemplary archaeon ssDNA-binding proteins described herein. ssDNA-binding proteins generally do not bind double-stranded DNA, or do so at a relatively low level compared with its binding of single-stranded DNA. The proteins usually comprise four DNA binding domains and typically comprise one or more zinc-containing domains which, due to their conformation, are known in the art as "zinc-fingers." Typically, ssDNA-binding proteins are 200 to 900 amino acids in length and more commonly are 500 to 800 amino acid residues in length. Archaeon ssDNA-binding proteins can be a multimer comprising two or more subunits, or can comprise a single polypeptide chain.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4: 11-17 (1988), e.g., as implemented in the program PC/GENE (Intelligenetics, Mountain View, Calif., USA).

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, *Proteins* (W. H. Freeman & Co., New York, N.Y. 1984)).

The phrase "substantially identical," in the context of two nucleic acids or polypeptides, refers to sequences or subsequences that have at least 60%, preferably 70%, more preferably 80%, even more preferably 90% and most preferably 95% or more nucleotide or amino acid residue identity when aligned for maximum correspondence over a comparison window as measured using one of the following sequence comparison algorithms or by manual alignment and visual inspection. With respect to nucleic acids, this definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1997) *Nucleic Acids Res.* 25: 3389-3402, respectively. Software for performing BLAST analyses is publicly available through the National Center for Biotechnology Information (found on the internet at "http://www." followed by "ncbi.nlm.nih.gov/"). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein or incorporated herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

Another indication that two nucleic acid sequences are substantially identical is that one of the two sequences hybridizes to the complement of the other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5-10° C. lower than the thermal melting point ($T_m$) for the specific sequence at a defined ionic strength and pH. Lower stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. In the present invention, genomic DNA or cDNA comprising nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

It is anticipated that conservative substitutions can be made in the nucleic acids taught herein which will permit expression of ssDNA-binding proteins functionally identical to those of the invention. It is further anticipated that conservative substitutions can be made in the amino acid sequence of the ssDNA-binding proteins themselves which still result in proteins of the desired robustness for use in PCR and other applications. These minor variations are fairly encompassed in the invention as described herein.

2. Nucleotide Sequences and Proteins with Sequence Identity to the Sequences Identified Herein Persons of skill in the art will recognize that the nucleotide sequences and protein sequences of the archaeon ssDNA-binding proteins identified herein can undergo substantial variation and still function as ssDNA-binding proteins. First, it will be recognized that, due to the degeneracy of the genetic code, the ssDNA-binding proteins identified herein can be encoded by large number of other nucleic acid sequences than the sequences determined from the genomes of the archaeons. Second, amino acid substitutions, and especially conservative substitutions, can be made in the proteins themselves without eliminating their ability to function as ssDNA-binding proteins. Third, persons of skill may wish to change the sequence of the protein to improve properties of the proteins, such as solubility, stability or DNA-binding, or to change the sequence of the nucleotides to improve, for example, yield of the protein when expressed in bacteria.

In general, nucleic acid sequences which encode ssDNA-binding proteins and having at least 70% sequence identity to SEQ ID NOS:2, 3, 4, 7, or 8 are encompassed by the present invention. More preferably, the nucleic acid sequences have 75%, 80%, or 85% sequence identity to SEQ ID NOS:2, 3, 4, 7, or 8, respectively. Even more preferably, the nucleic acid sequences have 90%, or 95% or even higher sequence identity to SEQ ID NOS:2, 3, 4, 7, or 8, respectively.

Similarly, ssDNA-binding proteins which have at least 70% sequence identity to SEQ ID NOS:1, 5, 6, 9, or 10, respectively, are encompassed by the present invention. More preferably, the proteins have 75%, 80%, or 85% sequence identity to SEQ ID NOS:1, 5, 6, 9, or 10, respectively. Even more preferably, the proteins have 90%, or 95% or even higher sequence identity to SEQ ID NOS:1, 5, 6, 9, or 10, respectively.

Any particular protein, such as the protein encoded by any particular nucleic acid, can be tested by standard assays to determine whether it functions as an ssDNA binding protein. Proteins which do not bind to ssDNA, and nucleic acid sequences encoding such proteins, are not within the scope of the present invention.

As noted, determinations of whether a particular protein binds DNA can be made by standard assays. Conveniently, such determinations can be made, for example, by agarose gel mobility shift assays with radioactively labeled single-stranded deoxythymidine-containing oligonucleotides. The oligonucleotides are incubated with increasing concentrations of a single-stranded DNA binding protein and then subjected to electrophoresis in an agarose gel to separate any protein-oligonucleotide complexes from free oligonucleotide. If the resulting bands show decreased mobility of oligonucleotides incubated with a higher concentration of the protein when compared to bands of oligonucleotides incubated with a lower concentration of protein, it indicates that a complex has formed between the oligonucleotide and the protein and thus that the protein has functioned as an ssDNA-binding protein. Details of performing such assays are taught, for example, by Kim et al., Biochemistry, 33:14197-206 (1994) and Kim et al., Mol. Cell Biol., 12:3050-3059.

If desired or necessary, binding competition studies can be conducted to confirm that the DNA binding protein binds single-stranded, not double-stranded, DNA. Conveniently, such assays can be performed by incubating reaction mixtures containing fixed amounts of the DNA binding protein and a radiolabeled deoxythymidine (dT) oligonucleotide with increasing concentrations of unlabeled single- or double-stranded DNA, such as M13. In the absence of sufficient amounts of the unlabeled DNA, most of the radiolabeled dT will form protein-DNA complexes. If the DNA binding protein binds single-stranded DNA, it will take significantly more double-stranded DNA to reduce the fraction of the radiolabeled dT in protein-DNA complexes by 50%. If the DNA binding protein binds double-stranded DNA, the reverse will be true. The assay can thus determine the relative affinity of the protein for each form of DNA.

E. Vectors, Host Cells Comprising Vectors, and Production of ssDNA Binding Proteins The ssDNA binding proteins of the invention can be prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding an ssDNA binding protein can be amplified by in vitro methods. Amplification methods include the polymerase chain reaction (PCR), the ligase chain reaction (LCR), the transcription-based amplification system (TAS), the self-sustained sequence replication system (3SR).

A wide variety of cloning methods, host cells, and in vitro amplification methodologies are well known to persons of skill.

In a preferred embodiment, an ssDNA binding protein is prepared by inserting the cDNA which encodes it into a vector. The insertion is made so that the an ssDNA binding protein are read in frame, that is, in one continuous polypeptide.

In addition to recombinant methods, ssDNA binding proteins can also be constructed in whole or in part using standard peptide synthesis. Solid phase synthesis of polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. *J. Am. Chem. Soc.* 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

Once the nucleic acids encoding an ssDNA binding protein of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, such as *Bacillus* or *Pseudomonas*, yeast, and various higher eukaryotic cells such as the COS, CHO, HeLa and myeloma cell lines. No attempt to describe in detail the various methods known for the expression of proteins in prokaryotes or eukaryotes will be made.

In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes. Expression of the proteins in prokaryotic cells, such as *E. coli*, is preferred.

F. An Evolutionary Model for ssDNA-Binding Proteins.

Alignment of the prokaryotic, archaeal and eukaryotic proteins that contain DNA-binding domain A reveals several features that are relevant to the evolution of ssDNA-binding proteins (see FIG. 4A). The N-terminal region of RPA70, which is involved in protein-protein interactions, is ~100 residues longer than that of *Methanococcus* RPA. This is expected, if we assume that a specific protein-protein-interaction domain was acquired late in evolution. The putative zinc-finger domain in RPA70 is also present in the archaeal protein, which argues for an early appearance of this motif. A zinc-finger is also found in the bacteriophage T4 ssDNA-binding protein, gene 32 protein, which shares little sequence homology with other ssDNA-binding proteins but retains considerable structural similarity (Smith, D. R. et al. *J. Bacteriol.* 179, 7135-7155 (1996)).

The structure of the archaeal protein offers some insights into a plausible succession of events linking the prokaryotic SSBs to their archaeal and eukaryotic counterparts. Gene amplification of a prokaryotic gene may have generated a protein that had several DNA-binding domains—as is the case for *M. jannaschii* and *M. thermoautotrophicum* (FIG. 4B). The N-terminal domain (which is involved in specific protein-protein interactions) and the C-terminal domain (which contains the zinc-finger motif) could have been acquired by gene fusion. Recombination between the partially homologous domains B and D would then produce a protein that was essentially similar to the RPA70 subunit, in that it had two DNA-binding domains and a conserved C-terminal region (FIG. 4B). This proposition is supported by the fact that the human RPA70 domain B shares the greatest degree of homology with the *M. jannaschii* MJ1159 domain D, while the RPA70 domain A is more similar to the MJ1159 domain A—thus reinforcing the idea that domains B and C were lost from RPA70.

If recombination between domains B and D was intramolecular and reciprocal, the reciprocal fragment could have been re-inserted into the genome by illegitimate recombination and therefore kept four ssDNA-binding sites available. Interestingly, such an organization corresponds closely to that described above for AF0382 and AF0780 in *A. fulgidus*, and could represent an intermediate gene organization that led ultimately to the emergence of eukaryotic RPAs. The RPA32 and RPA14 subunits would then have arisen after a final step of gene separation (FIG. 4B).

Note that although the pathway depicted in FIG. 4B starts with the prokaryotic SSB, we do not imply that bacterial SSBs correspond to the ancestral protein; it is equally plausible that the bacterial proteins arose from an ancestor rooted in the archaeal tree, by a process that is the reverse of the first step shown in FIG. 4B.

Together, these data strongly suggest that ssDNA-binding proteins in the Archaea belong to a class of previously undescribed DNA-binding proteins whose architecture might represent the missing evolutionary link between the prokaryotic and the eukaryotic SSB proteins. The presence of RPA-related proteins in archaeal organisms indicates that, despite the extreme environmental conditions typical of their natural habitats (e.g., high temperatures), their chromosomal DNA is likely to be stabilized in a double-stranded form and, hence, that the need for such proteins has been conserved. Archaeal RPA homologues, like their bacterial and eukaryotic counterparts, are probably involved in maintaining DNA in a transient single-stranded form, protecting this single-stranded DNA from nucleases and promoting important protein-protein contacts.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A mixture of polymerase chain reaction ("PCR") reactants, the mixture comprising:
   (a) an ssDNA-binding protein having at least 90% sequence identity to SEQ ID NO:1, which protein is an oligonucleotide/oligosaccharide binding (OB)-fold protein that: (i) comprises four ssDNA-binding protein domains, said domains having a channel so sized as to permit binding of ssDNA along the channel; (ii) comprises at least one zinc finger domain in the carboxyl portion of the protein, which zinc finger domain comprises at least four cysteines; and (iii) binds single stranded DNA; and
   (b) a DNA polymerase.

2. A mixture of claim 1, wherein the ssDNA binding protein has at least 95% sequence identity to the amino acid sequence of SEQ ID NO:1.

3. A mixture of claim 2, wherein the ssDNA binding protein has the amino acid sequence of SEQ ID NO:1.

4. A mixture of claim 1, wherein the DNA polymerase is present at a concentration of 0.02 units/ul.

5. A method of assembling a reaction mixture for a polymerase chain reaction, comprising the steps of:
   (a) providing an ssDNA-binding protein having at least 90% sequence identity to SEQ ID NO:1, which protein is an oligonucleotide/oligosaccharide binding (OB)- fold protein that: (i) comprises four ssDNA-binding protein domains, said domains having a channel so sized as to permit binding of ssDNA along the channel; (ii) comprises at least one zinc finger domain in the carboxyl portion of the protein, which zinc finger domain comprises at least four cysteines; and (iii) binds single stranded DNA; and (b) mixing a DNA polymerase with the ssDNA-binding protein to produce the reaction mixture.

6. A method of claim 5, wherein the ssDNA binding protein has at least 95% sequence identity to the amino acid sequence of SEQ ID NO:1.

7. A method of claim 5, wherein the ssDNA binding protein has the amino acid sequence of SEQ ID NO:1.

8. A method of claim 5 wherein the mixture of PCR reactants comprises the DNA polymerase at a concentration of 0.02 units/ul.

* * * * *